(12) United States Patent
Astary et al.

(10) Patent No.: US 11,940,515 B2
(45) Date of Patent: Mar. 26, 2024

(54) SYSTEM, METHOD AND COMPUTER-READABLE MEDIUM FOR EVALUATING STRUCTURAL INTEGRITY OF A GRADIENT COIL

(71) Applicant: GE PRECISION HEALTHCARE LLC, Wauwatosa, WI (US)

(72) Inventors: Garrett William Astary, Silver Spring, MD (US); Derek Seeber, Florence, SC (US); Andrew John Panos, Brookfield, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 99 days.

(21) Appl. No.: 17/587,252

(22) Filed: Jan. 28, 2022

(65) Prior Publication Data

US 2022/0146608 A1 May 12, 2022

Related U.S. Application Data

(63) Continuation-in-part of application No. 15/974,323, filed on May 8, 2018, now Pat. No. 11,269,749.

(51) Int. Cl.
*G01V 3/00* (2006.01)
*A61B 5/055* (2006.01)
*G01R 33/385* (2006.01)
*G01R 35/00* (2006.01)

(52) U.S. Cl.
CPC ........... *G01R 33/385* (2013.01); *A61B 5/055* (2013.01); *G01R 35/00* (2013.01); *A61B 2560/0276* (2013.01)

(58) Field of Classification Search
CPC ............. G01R 33/3415; G01R 33/543; G01R 33/5659; G01R 33/36; A61B 5/055
USPC ........................................................ 324/301
See application file for complete search history.

(56) References Cited

U.S. PATENT DOCUMENTS

| 8,373,417 | B2 | 2/2013 | Nerreter |
| 8,373,471 | B2 | 2/2013 | Kim et al. |
| 2003/0215125 | A1 | 11/2003 | Yokoi et al. |
| 2005/0156596 | A1* | 7/2005 | Havens ............... G01R 33/3854 324/318 |
| 2011/0184250 | A1 | 7/2011 | Schmidt et al. |
| 2013/0303870 | A1 | 11/2013 | Satish et al. |
| 2015/0369888 | A1 | 12/2015 | Calvert |
| 2016/0178713 | A1 | 6/2016 | Fischer et al. |
| 2016/0327606 | A1 | 11/2016 | Van Wieringen |
| 2016/0328852 | A1* | 11/2016 | Beall .................. G06N 7/01 |
| 2017/0059670 | A1 | 3/2017 | Gebhardt et al. |

(Continued)

FOREIGN PATENT DOCUMENTS

CN 104237818 A * 12/2014
WO WO-2017018755 A1 * 2/2017 ............. B63B 22/16

*Primary Examiner* — Walter L Lindsay, Jr.
*Assistant Examiner* — Frederick Wenderoth
(74) *Attorney, Agent, or Firm* — Grogan, Tuccillo & Vanderleeden LLP

(57) ABSTRACT

A system, method, and computer-readable medium for evaluating structural integrity of a gradient coil disposed in a magnetic resonance imaging system is provided. A sensor obtains a parameter reading of the gradient coil, wherein the parameter reading includes a back electromotive force (back EMF) measurement. The structural integrity of the gradient coil is determined as function of the back EMF measurement.

18 Claims, 16 Drawing Sheets

(56) References Cited

U.S. PATENT DOCUMENTS

2017/0146677 A1     5/2017   Song et al.
2017/0307702 A1   10/2017   Kanakasabai et al.
2017/0336483 A1   11/2017   Cunningham

* cited by examiner

SYSTEM, METHOD AND COMPUTER-READABLE MEDIUM FOR EVALUATING STRUCTURAL INTEGRITY OF A GRADIENT COIL

CROSS-REFERENCE TO RELATED APPLICATIONS

The present patent application is a continuation-in-part of U.S. application Ser. No. 15/974,323, filed 8 May 2018, of which is hereby incorporated by reference in its entirety to provide continuity of disclosure.

TECHNICAL FIELD

This disclosure relates to a system, a method and a computer-readable medium for monitoring a health status of a gradient coil disposed in a magnetic resonance imaging system, and more particularly, to evaluating the structural integrity of the gradient coil.

DISCUSSION OF ART

Magnetic resonance imaging ("MRI") is a widely accepted and commercially available technique for obtaining digitized visual images representing the internal structure of objects having substantial populations of atomic nuclei that are susceptible to nuclear magnetic resonance ("NMR"). Many MRI systems use superconductive magnets to scan a subject/patient via imposing a strong main magnetic field on the nuclei in the subject. The nuclei are excited by a radio frequency ("RF") signal/pulse transmitted by a RF coil at characteristics NMR (Larmor) frequencies. By spatially disturbing localized magnetic fields surrounding the subject and analyzing the resulting RF responses, also referred to hereinafter as the "MR signal," from the nuclei as the excited protons relax back to their lower energy normal state, a map or image of these nuclei responses as a function of their spatial location is generated and displayed. An image of the nuclei responses, also referred to hereinafter as an "MRI image" and/or simply "image," provides a non-invasive view of a subject's internal structure.

Many MRI systems utilize large electromagnetic coils, commonly referred to as gradient coils, to generate magnetic gradient fields within a target volume containing the subject by exciting/energizing the gradient coils via an electrical current. Continued/repeated excitation of a gradient coil over an extended period of time, however, may damage the gradient coil, which in turn, may result in failure of the gradient coil, e.g., generation of degraded magnetic gradient fields and/or an inability to generate a magnetic gradient field at all. Typically, failure of a gradient coil results in unusable data from an MRI procedure/scan. As will be appreciated, many MRI procedures are often resource intensive. Thus, executing an MRI procedure/scan with an undetected failed gradient coil is often a costly event for both patients and MRI system operators, e.g., hospitals. Additionally, structural failure of the gradient coil may lead to increased sound pressure levels emitted by the gradient coil resulting in patient discomfort or, potentially, deleterious impacts on patient hearing.

Due to a variety of reasons, it is often difficult and/or impossible to predict when a particular gradient coil will fail via manual inspection. For example, gradient coils can be difficult to manually inspect as they are typically located/encased in a magnet assembly. As such, manual inspection of a gradient coil typically requires the MRI system to be taken offline, i.e., out of service, which reduces the availability of the MRI system to patients. Further, manual inspection of a gradient coil may not accurately predict failure of the gradient coil as many traditional gradient coil diagnostics systems are limited in their capabilities to detect/recognize symptoms indicative of an impending failure. While automated approaches for detecting a failed gradient coil exist, many such approaches are only effective after failure of the gradient coil has occurred. Additionally, such systems may be limited in their capabilities to detect/recognize symptoms indicative of an impending failure.

Thus, an improved system and method for monitoring a health status of a gradient coil disposed in an MRI system is generally desired.

BRIEF DESCRIPTION

In an embodiment, the present disclosure provides for a system for monitoring a health status of a gradient coil disposed in a magnetic resonance imaging system. The system includes one or more sensors and a controller. The one or more sensors are operative to obtain one or more parameter readings of the gradient coil, wherein the one or more parameter readings include at least one of an acoustic measurement and a back electromotive force measurement. The controller is in electronic communication with the one or more sensors and operative to generate the health status based on at least one of the acoustic measurement and the back electromotive force measurement.

In another embodiment, the present disclosure provides for a method for monitoring a health status of a gradient coil in a magnetic resonance imaging system. The method includes obtaining one or more parameter readings of the gradient coil via one or more sensors, wherein the one or more parameter readings include at least one of an acoustic measurement and a back electromotive force measurement. The method further includes generating, with a controller in electronic communication with the one or more sensors, the health status based on at least one of the acoustic measurement and the back electromotive force measurement.

In yet another embodiment, the present disclosure provides for a method of training a neural network. The method includes feeding a training dataset to the neural network. The training dataset includes a plurality of pairings each comprising of a parameter reading and a known health status of a gradient coil, wherein the parameter reading is at least one of an acoustic measurement and a back electromotive force measurement. The method further includes training the neural network in a supervised manner on the training dataset such that, for one or more of the pairings, the neural network generates a health status that substantially matches the known health status. The method further includes outputting, after the neural network has been trained, one or more weights of the neural network.

In yet another embodiment, the present disclosure provides for a system for monitoring a health status of a gradient coil. The system includes a sensor and a controller. The sensor is operative to obtain one or more parameter readings of the gradient coil. The controller is in electronic communication with the sensor and operative to generate the health status based at least in part on the one or more parameter readings.

DRAWINGS

Various aspects of this disclosure may be better understood upon reading the following detailed description and upon reference to the drawings in which.

Figure 19:
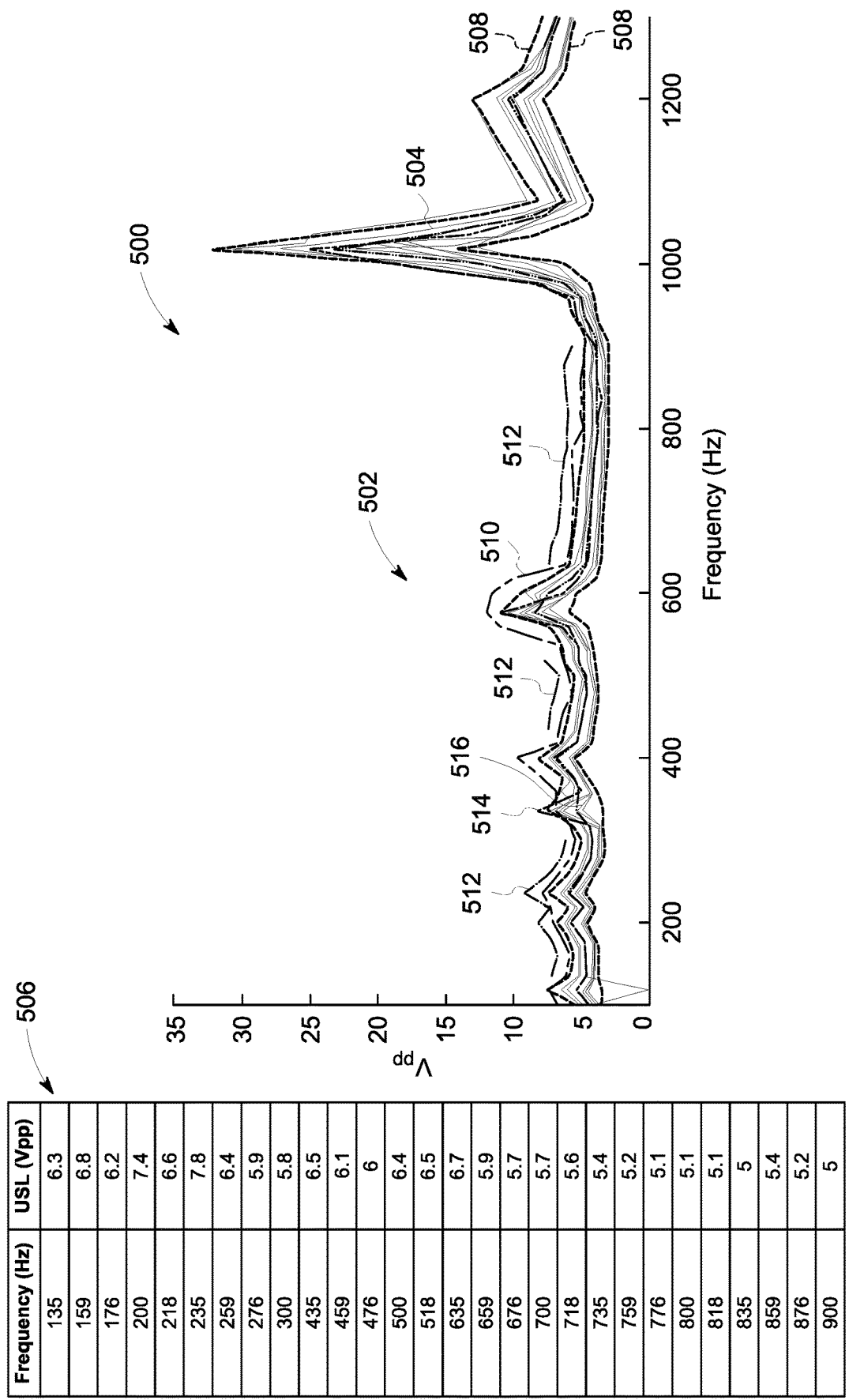
Figure 20:
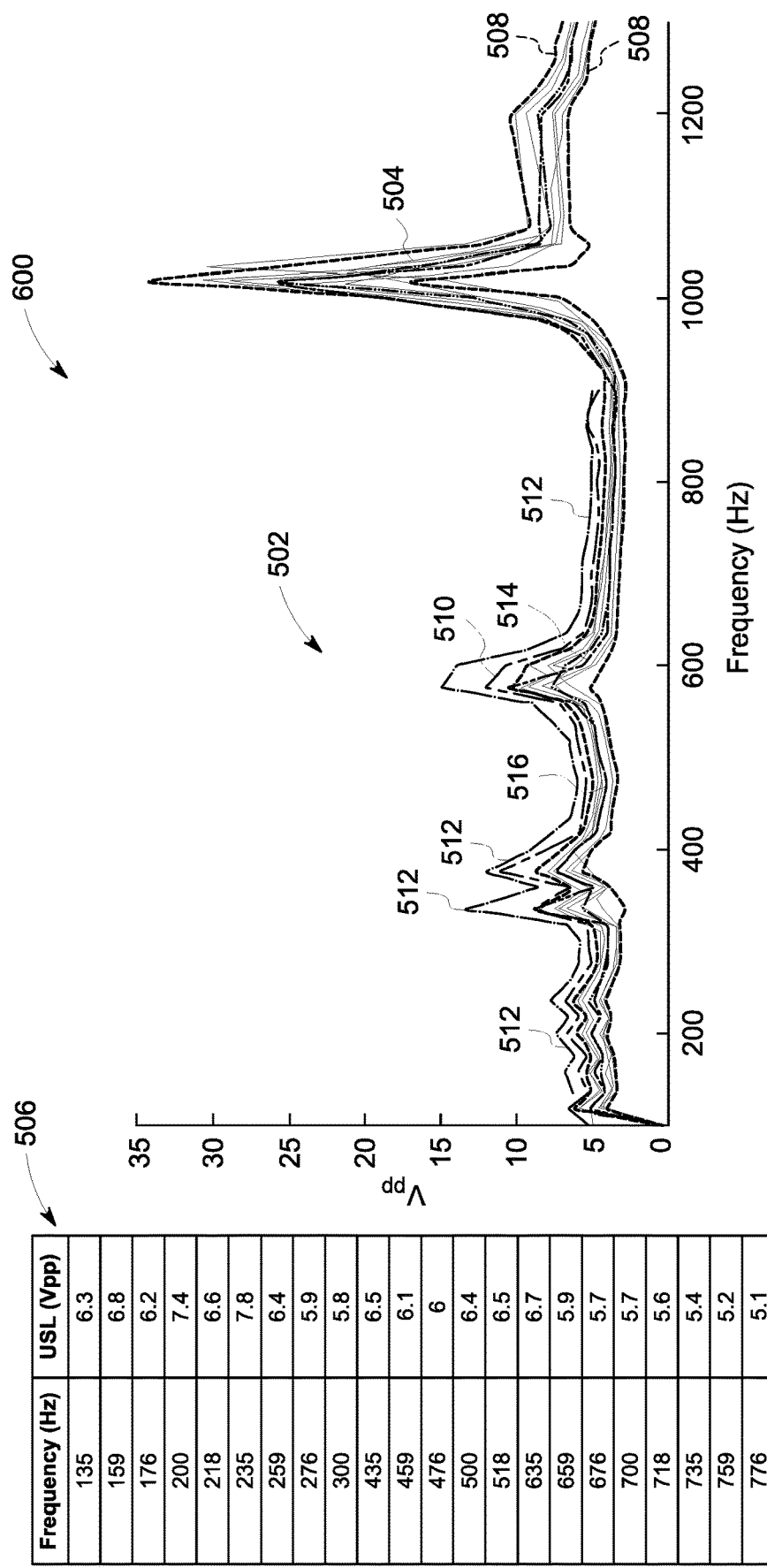

FIG. 19 is an example illustrating an evaluation of the structural integrity of a gradient coil using acceptance criteria that excludes back EMF measurements that correspond with regions near mechanical resonance frequencies of the gradient coil, in accordance with an exemplary embodiment; and FIG. 20 is an example illustrating an evaluation of the structural integrity of a gradient coil using acceptance criteria that includes back EMF measurements that correspond with regions of mechanical resonance frequencies of the gradient coil and regions that are between mechanical resonance frequencies, in accordance with an exemplary embodiment.

The drawings illustrate specific aspects of the described systems and methods for monitoring a health status of a gradient coil. Together with the following description, the drawings demonstrate and explain the principles of the structures, methods, and principles described herein. In the drawings, the size of the components may be exaggerated or otherwise modified for clarity. Well-known structures, materials, or operations may not be shown or described in detail to avoid obscuring aspects of the described components, systems, and methods.

DETAILED DESCRIPTION

One or more specific embodiments of the present disclosure are described below in order to provide a thorough understanding. These described embodiments are only examples of systems and methods for monitoring a health status of a gradient coil. Moreover, as will be understood, embodiments of the invention are not limited to neural networks and, accordingly, may include other forms of artificial intelligence. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

In addition, it should be understood that references to "one embodiment" or "an embodiment" of the present disclosure are not intended to be interpreted as excluding the existence of additional embodiments that also incorporate the recited features. Further, the limitations of the following claims are not written in means-plus-function format and are not intended to be interpreted as such, unless and until such claim limitations expressly use the phrase "means for" followed by a statement of function void of further structure.

Further, it is to be understood that embodiments of the present invention may be applicable to Positron Emission Tomography ("PET")/MRIs and/or any other system having components susceptible to failure and/or degraded performance resulting from stresses incurred from use. For example, while the present invention is discussed herein as monitoring the health status of a gradient coil, it is to be understood that the systems and methods disclosed herein are equally applicable to other components in an MRI system, e.g., body coils, superconductive magnets, gradient amplifiers, etc.

Referring to the figures generally, the present disclosure is to provide systems and methods for monitoring a health status of a gradient coil disposed in an MRI system. In some embodiments, the systems and methods disclosed herein generate a health status of a gradient coil based on statistical deviation between one or more parameter readings of the gradient coil and the historical norms of the same parameters readings of gradient coils that have experienced little to no structural degradation. The term "parameter reading", as used herein with respect to a gradient coil, refers to a measurement of a physical and/or chemical characteristic/metric of a gradient coil The parameter readings may be of various metrics of a gradient coil such as acoustics, e.g., sound waves, back electromotive force ("back EMF") measurements, and/or other metrics related to the structural degradation of a gradient coil. As used herein, the terms "back electromotive force" and "back EMF" refer to a counter-electromotive force generated in a gradient coil after removal of an applied excitation current. The term "structural degradation", as used herein with respect to a gradient coil, refers to changes in the physical and/or chemical structure of the materials forming the gradient coil.

In some embodiments, the controller may generate the health status based on a pre-determined/known correlation/scale/model that maps/correlates one or more statistical differences/variances of gradient coil parameter readings from historical norms to known levels/amounts of gradient coil structural degradation. In embodiments, the correlation between statistical deviations in parameter readings and structural degradation may be determined in part by passing parameter readings obtained from one or more gradient coils to a neural network, i.e., the neural network may be trained on a historical dataset of parameter readings acquired from the gradient coils of multiple MRI systems. By analyzing a dataset of historical parameter readings, the neural network of some embodiments is able to provide an accurate indication of the health status of a gradient coil based on new parameter readings acquired from the gradient coil. Thus, in some embodiments, the controller may generate a health status for a gradient coil by passing/feeding parameter readings acquired from the gradient coil to a neural network. Additionally, in some embodiments, the controller and/or neural network is able to predict a time period during which the gradient coil may be expected to fail.

Figure 1:
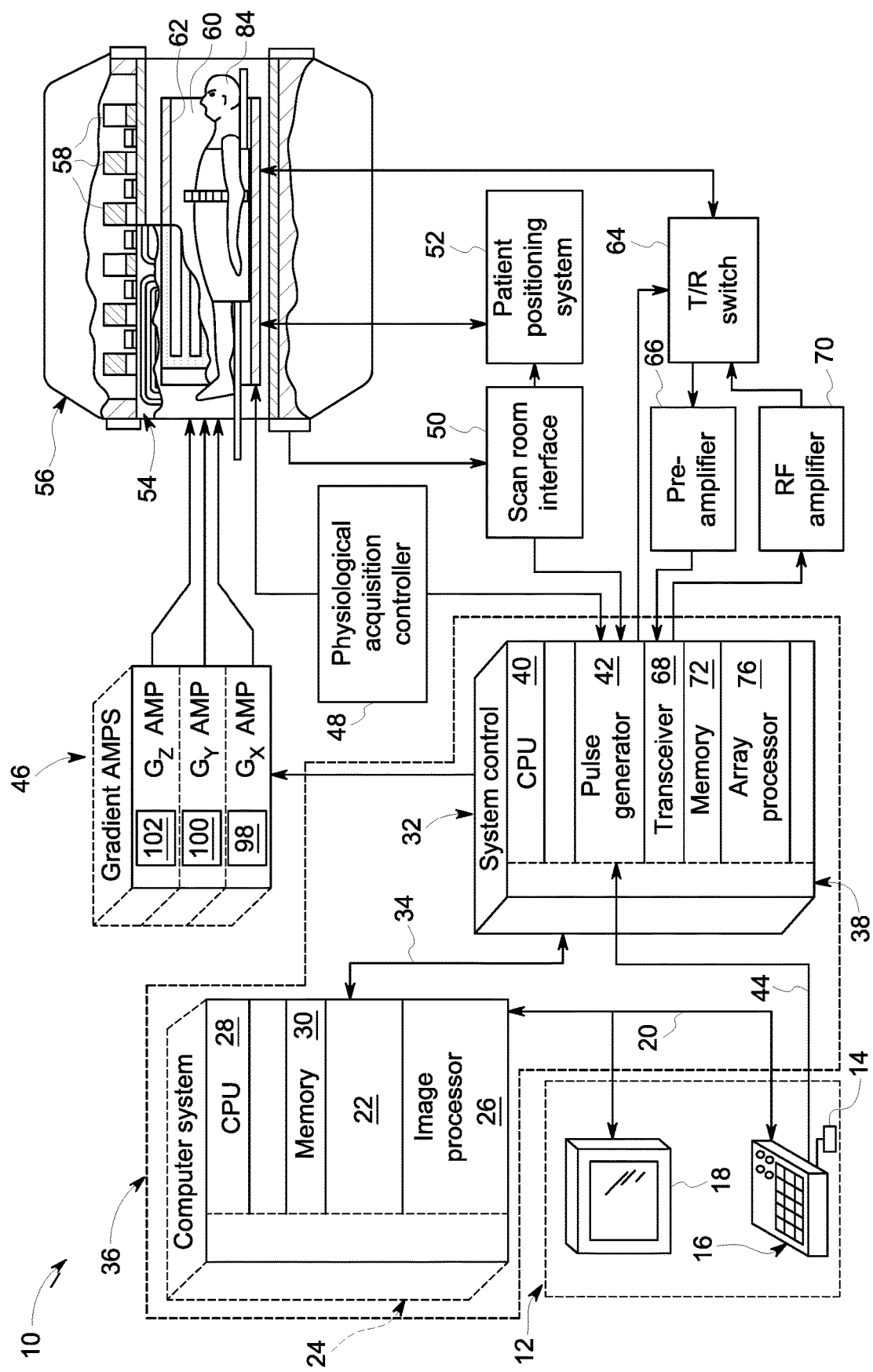
FIG. 1 is a block diagram of an MRI system that includes a system for monitoring a health status of a gradient coil, in accordance with an exemplary embodiment.

Now referring to FIG. 1, the major components of an MRI system 10 incorporating an exemplary embodiment of the invention are shown. Accordingly, operation of the system 10 is controlled from the operator console 12, which includes a keyboard or other input device 14, a control panel 16, and a display screen 18. The console 12 may communicate through a link 20 with a separate computer system 22 that enables an operator to control the production and display of images on the display screen 18. The computer system 22 may include a number of modules, which communicate with each other through a backplane 24. In embodiments, these include an image processor module 26, a CPU module 28, and a memory module 30, which may include a frame buffer for storing image data arrays. The computer system 22 may communicate with a separate system control or control unit 32 through a high-speed serial link 34. The input device 14 can include a mouse, joystick, keyboard, track ball, touch activated screen, light wand, voice control, or any similar or equivalent input device, and may be used for interactive geometry prescription. The computer system 22 and the MRI system control 32 collectively form an "MRI controller" 36.

In embodiments, the MRI system control 32 includes a set of modules connected together by a backplane 38. These include a CPU module 40 and a pulse generator module 42, which connects to the operator console 12 through a serial link 44. It is through link 44 that the system control 32 receives commands from the operator to indicate the scan sequence that is to be performed. The pulse generator module 42 operates the system components to execute the desired scan sequence and produces data which indicates the timing, strength and shape of the RF pulses produced, and the timing and length of the data acquisition window. The pulse generator module 42 connects to a set of gradient amplifiers 46, to indicate the timing and shape of the gradient pulses that are produced during the scan. The pulse generator module 42 can also receive patient data from a physiological acquisition controller 48 that receives signals from a number of different sensors connected to the patient, such as ECG signals from electrodes attached to the patient. And finally, the pulse generator module 42 connects to a scan room interface circuit 50, which receives signals from various sensors associated with the condition of the patient and the magnet system. It is also through the scan room interface circuit 50 that a patient positioning system 52 receives commands to move the patient to the desired position for the scan.

The pulse generator module 42 operates the gradient amplifiers 46 to achieve desired timing and shape of the gradient pulses that are produced during the scan. The gradient waveforms produced by the pulse generator module 42 are applied to the gradient amplifier system 46 having Gx, Gy, and Gz amplifiers. Each gradient amplifier excites a corresponding physical gradient coil in a gradient coil assembly, generally designated 54, to produce the magnetic field gradients used for spatially encoding acquired signals. The gradient coil assembly 54 forms part of a magnet assembly 56, which also includes a polarizing magnet 58 (which in operation, provides a homogenous longitudinal magnetic field $B_0$ throughout a target volume 60 that is enclosed by the magnet assembly 56) and a whole-body (transmit and receive) RF coil 62 (which, in operation, provides a transverse magnetic field $B_1$ that is generally perpendicular to $B_0$ throughout the target volume 60).

The resulting signals emitted by the excited nuclei in the patient may be sensed by the same RF coil 62 and coupled through the transmit/receive switch 64 to a preamplifier 66. The amplifier MR signals are demodulated, filtered, and digitized in the receiver section of a transceiver 68. The transmit/receive switch 64 is controlled by a signal from the pulse generator module 42 to electrically connect an RF amplifier 70 to the RF coil 62 during the transmit mode and to connect the preamplifier 66 to the RF coil 62 during the receive mode. The transmit/receive switch 64 can also enable a separate RF coil (for example, a surface coil) to be used in either transmit or receive mode.

The MR signals picked up by the RF coil 62 are digitized by the transceiver module 68 and transferred to a memory module 72 in the system control 32. A scan is complete when an array of raw K-Space data has been acquired in the memory module 72. This raw K-Space data/datum is rearranged into separate K-Space data arrays for each image to be reconstructed, and each of these is input to an array processor 76 which operates to Fourier transform the data into an array of image data. This image data is conveyed through the serial link 34 to the computer system 22 where it is stored in memory 30. In response to commands received from the operator console 12, this image data may be archived in long-term storage or it may be further processed by the image processor 26, conveyed to the operator console 12, and presented on the display 18.

Figure 2:
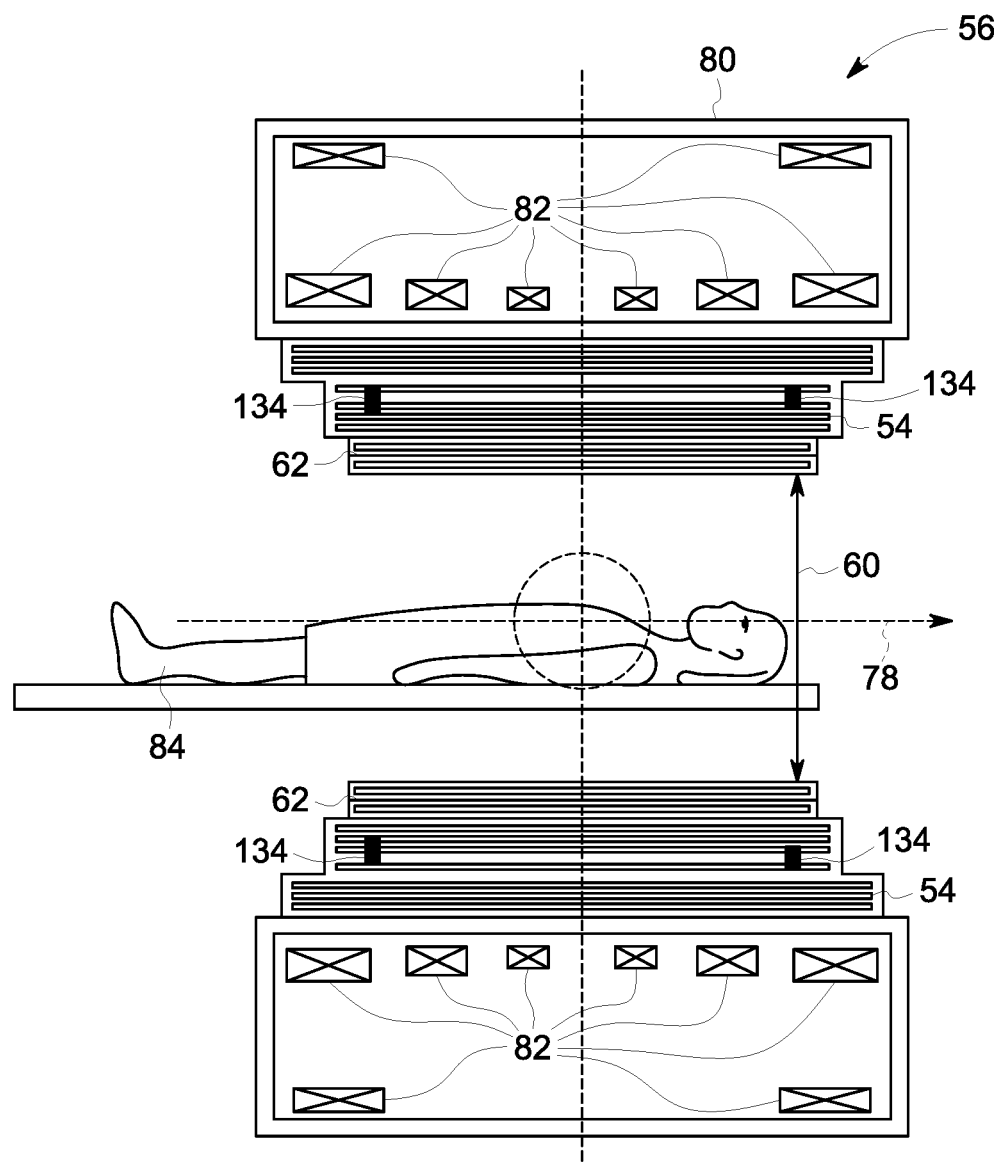
FIG. 2 is a schematic cross-sectional diagram of a magnet assembly of the MRI system of FIG. 1, in accordance with an exemplary embodiment.

As illustrated in FIG. 2, a schematic side elevation view of the magnet assembly 56 is shown in accordance with an embodiment of the invention. The magnet assembly 56 is cylindrical in shape having a center/central axis 78. The magnet assembly 56 includes a cryostat 80 and one or more radially aligned longitudinally spaced apart superconductive coils 82 that form the polarizing magnet 58 (FIG. 1). The superconductive coils 82 are capable of carrying large electrical currents and are designed to create the $B_0$ field within the patient/target volume 60. As will be appreciated, the magnet assembly 56 may further include both a terminal shield and a vacuum vessel (not shown) surrounding the cryostat 80 in order to help insulate the cryostat 80 from heat generated by the rest of the MRI system 10 (FIG. 1). The magnet assembly 56 may still further include other elements such as covers, supports, suspension members, end caps, brackets, etc. (not shown). While the embodiment of the magnet assembly 56 shown in FIGS. 1 and 2 utilizes a cylindrical topology, it should be understood that topologies other than cylindrical may be used. For example, a flat geometry in a split-open MRI system may also utilize embodiments of the invention described below. As further shown in FIG. 2, a patient/imaged subject 84 is inserted into the magnet assembly 56.

Figure 3:
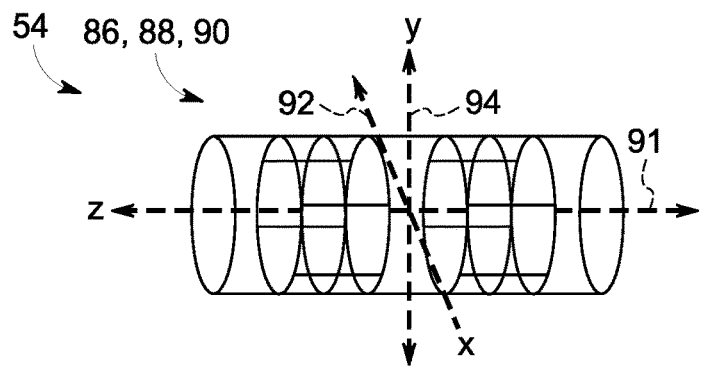
FIG. 3 is a diagram of a gradient coil assembly of the magnet assembly of FIG. 2, in accordance with an exemplary embodiment.

Illustrated in FIGS. 3-6 are various gradient coils 86, 88, and 90 of the gradient coil assembly 54 (FIG. 3). As will be understood, in embodiments, the gradient coil assembly 54 may include an x-gradient coil 86 (best seen in FIG. 4) operative to generate/apply a gradient magnetic field along/corresponding to an x-axis 92, a y-gradient coil 88 (best seen in FIG. 5) operative to generate/apply a gradient magnetic field along/corresponding to a y-axis 94, and a z-gradient coil 90 (best seen in FIG. 6) operative to generate/apply a gradient magnetic field along/corresponding to a z-axis 91, which may be the same as the central axis 78 (FIG. 2) of the magnet assembly 56 (FIGS. 1 and 2). As will be appreciated, in addition to applying magnetic gradients oriented along the axes 91, 92, and 94, the gradient coils 86, 88, and 90 may be utilized to apply magnetic gradients along/corresponding to any direction within the space defined by the three axes 91, 92, and 94.

Figure 6:
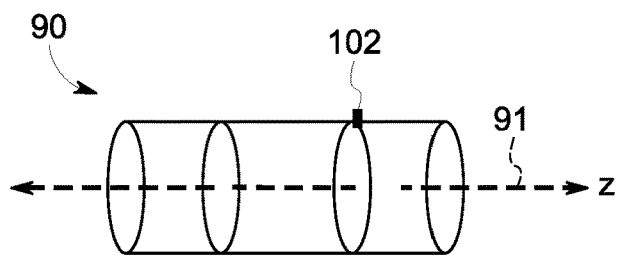
FIG. 6 is a diagram of a z-axis gradient coil of the gradient coil assembly of FIG. 3, in accordance with an exemplary embodiment.
Figure 7:
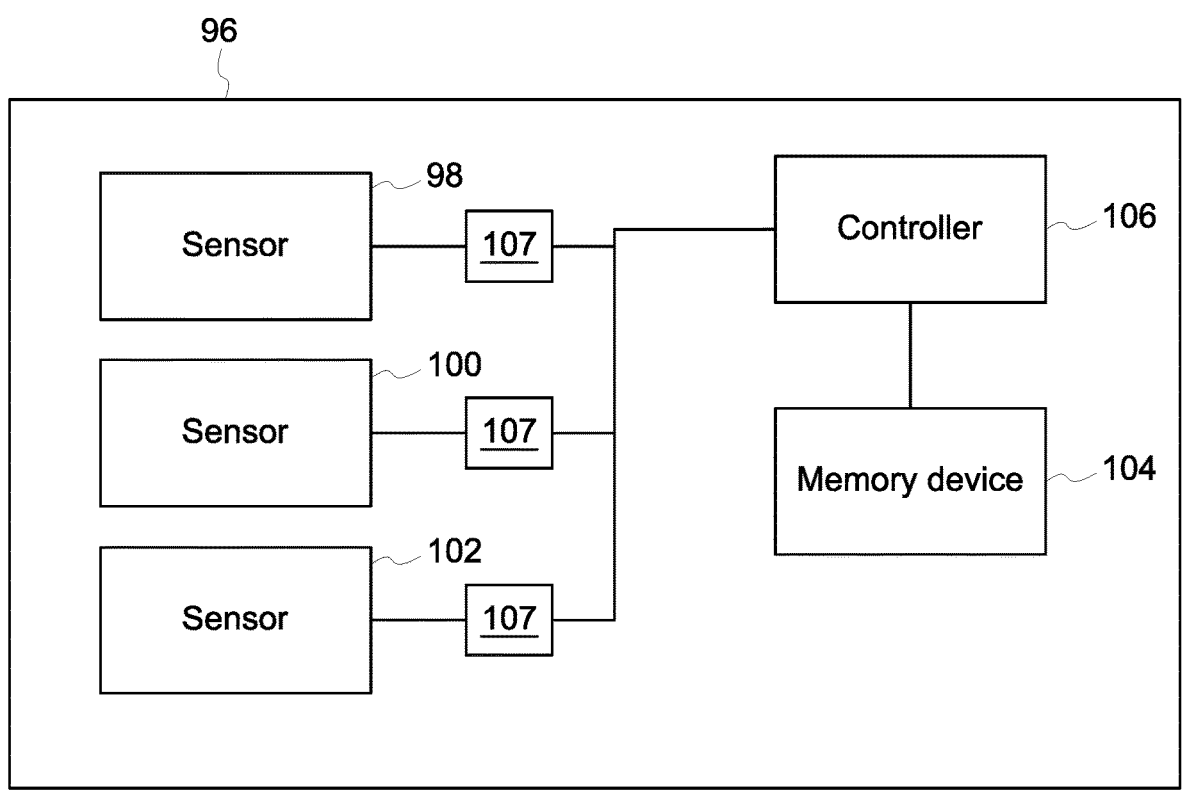
FIG. 7 is a block diagram of the system for monitoring a health status of a gradient coil disposed in the MRI system of FIG. 1, in accordance with an exemplary embodiment.

Turning to FIG. 7, a system 96 for monitoring a health status of a gradient coil 86, 88, and/or 90 (FIGS. 4-6) according to an exemplary embodiment of the invention is shown. The system 96, which, in embodiments, may be incorporated into the MRI system 10 (FIGS. 1 and 2), includes one or more sensors 98, 100, 102 (also shown in FIGS. 1 and 4-6), a memory device 104 (optionally), and a controller 106. The one or more sensors 98, 100, 102 are operative to obtain one or more parameter readings 107 of the gradient coil 86, 88, and/or 90, and the memory device 104 may store a neural network 108 (FIG. 12) and/or other types of models. Although three (3) sensors 98, 100, 102 are depicted in FIGS. 1 and 4-7, it will be understood that the invention is not limited to three (3) sensors and that embodiments may include fewer and or greater than three (3) sensors.

The controller 106 is in electronic communication with the one or more sensors 98, 100, 102, the memory device 104, and is operative/configured/adapted to generate a health status 110 (FIG. 14) that provides an indication of structural degradation of the gradient coil 86, 88, and/or 90. As will be understood, in embodiments, the memory device 104 may be separate from, or include, memory devices 30 and/or 72 (FIG. 1). Similarly, the controller 106 may be separate from, or include, controller 36 (FIG. 1).

Figure 4:
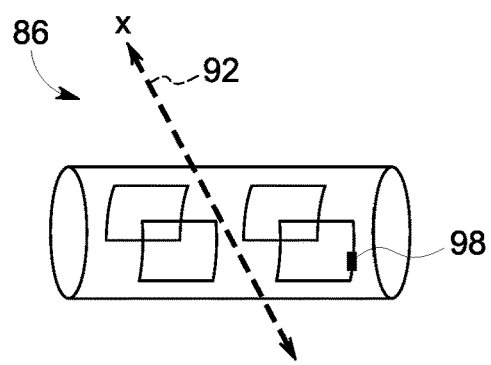
FIG. 4 is a diagram of an x-axis gradient coil of the gradient coil assembly of FIG. 3, in accordance with an exemplary embodiment.
Figure 5:
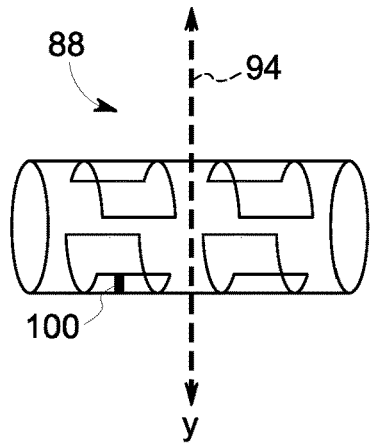
FIG. 5 is a diagram of a y-axis gradient coil of the gradient coil assembly of FIG. 3, in accordance with an exemplary embodiment.

As best seen in FIGS. 4-6, the one or more sensors 98, 100, 102 may be disposed proximate to, i.e., close, touching, and/or within, the gradient coil 86, 88, and/or 90. In embodiments, the obtained parameter readings 107 may include acoustic measurements and/or back EMF measurements.

For example, in certain embodiments, one or more of the sensors 98, 100, 102 may be a microphone, e.g., a condenser or optical microphone, that acquires acoustic measurements which may be of frequency, amplitude, or other sound-based metrics, generated by the gradient coil 86, 88, and/or 90. As will be understood, the acoustics of a gradient coil 86, 88, and/or 90 change as the level/amount of structural degradation of the coil 86, 88, and/or 90 changes. Thus, by mapping acoustics sampled from a gradient coil 86, 88, and/or 90 to known levels of structural degradation, embodiments of the present invention create a model, e.g., a neural network, that can be used to find the structural degradation of other gradient coils based on their acoustics.

Figure 8:
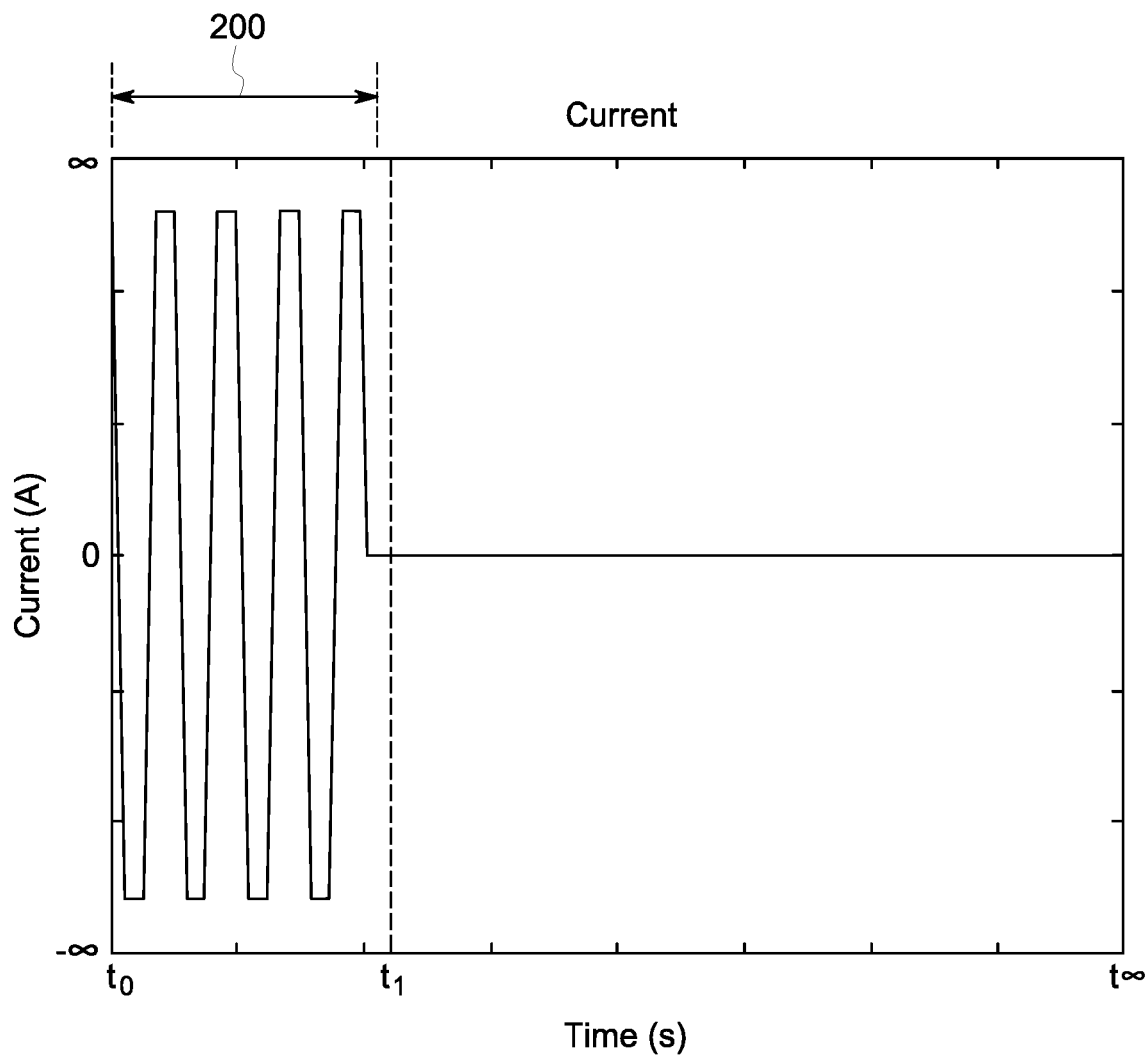
FIG. 8 is a chart depicting an excitation current applied to a gradient coil of the gradient coil assembly of FIG. 3, in accordance with an exemplary embodiment.
Figure 9:
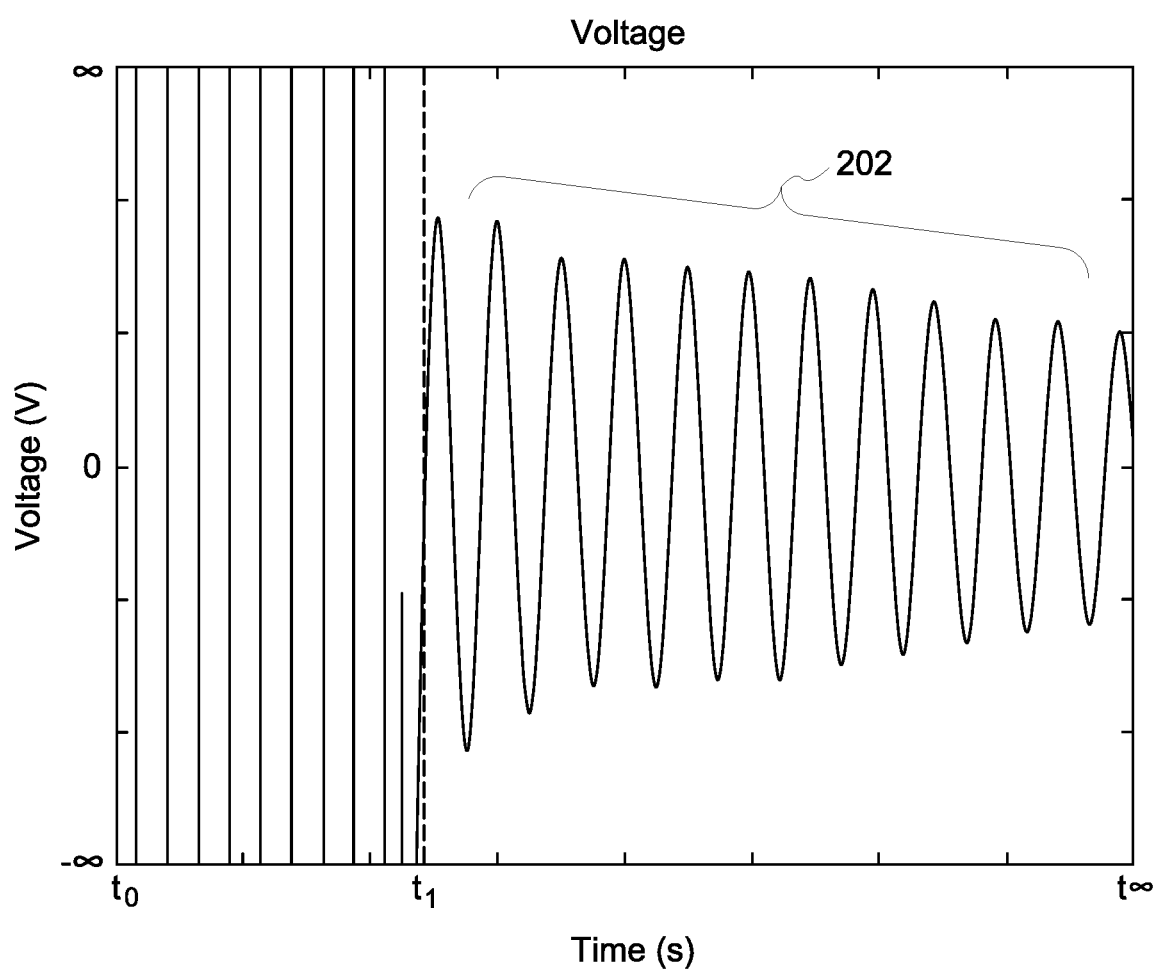
FIG. 9 is a chart depicting a back EMF voltage induced in the gradient coil after application of the excitation current of FIG. 8, in accordance with an exemplary embodiment.

Referring now to FIGS. 8 and 9, as stated above, in embodiments, the one or more sensors 98, 100, and 102 may obtain a back EMF measurement of a gradient coil 86, 88, and/or 90. As shown in FIGS. 8 and 9, in embodiments, a gradient amplifier 46 (FIG. 1) may apply and remove an excitation current 200 (FIG. 8) to a gradient coil 86, 88, and/or 90 (FIGS. 4-6), where the back EMF measurement is of a voltage 202 (FIG. 9), also referred to herein as a "back EMF voltage", induced by the movement of the gradient coil 86, 88, and/or 90 within the $B_0$ magnetic field. In embodiments, the excitation current 200 may be an AC current with the back EMF voltage 202 occurring due to the Lorentz force in gradient coil 86, 88, and/or 90 deformations, i.e., movement of the coil 86, 88, and/or 90 through the $B_0$ field lines, with the coil 86, 88, and/or 90 eventually settling back to equilibrium, i.e., no movement through the $B_0$ field lines. As will be understood, the greater the structural degradation of a gradient coil 86, 88, and/or 90, the greater the displacement/movement of the coil 86, 88, and/or 90 through the $B_0$ field lines, and, as a result, the greater the back EMF voltage 202 induced in the coil 86, 88, and/or 90. For example, as shown in FIGS. 8 and 9, the gradient amplifier 46 may apply an excitation current 200 for a period of time, e.g., $t_0$ to $t_1$, which, in turn, results in the back EMF voltage 202 being induced in a decaying manner after removal of the excitation current 200 at $t_1$, i.e., the oscillations of the sine wave of the voltage 202 decay/shrink over time as the coil 86, 88, and/or 90 returns back to equilibrium.

Figure 10:
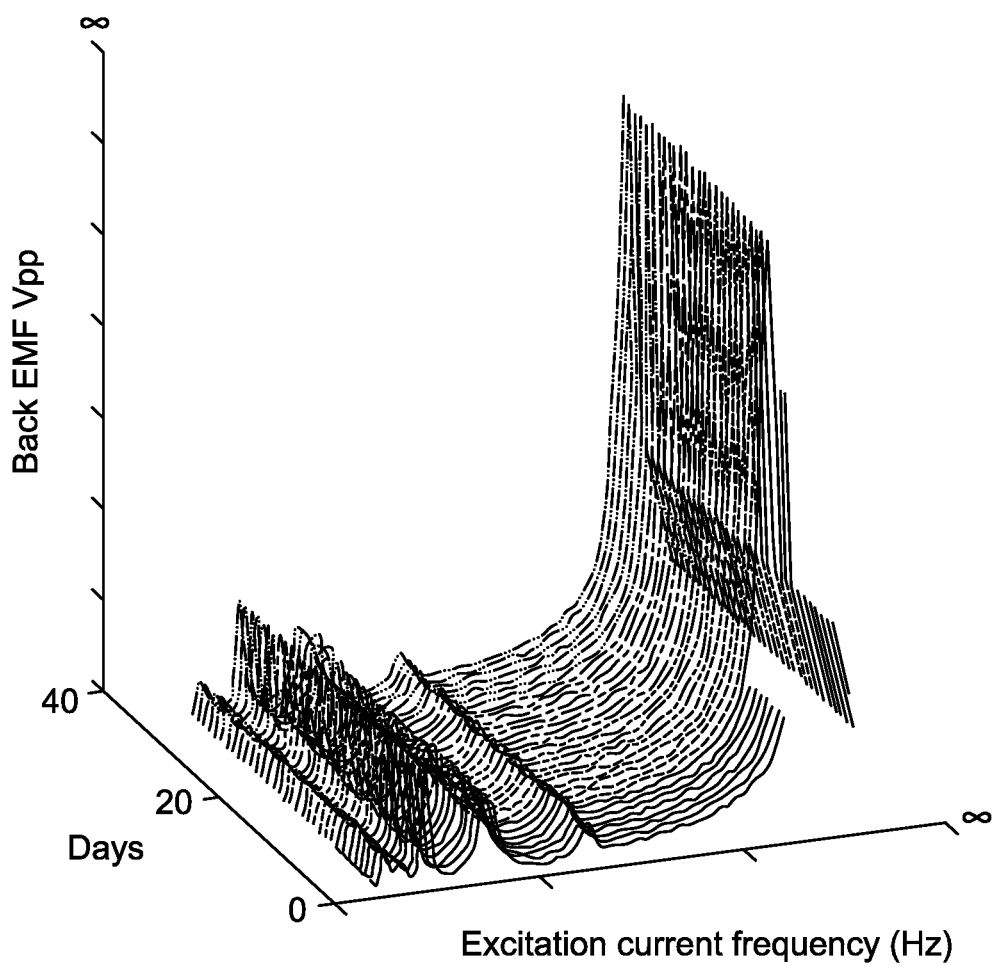
FIG. 10 is a chart depicting peak back EMF voltages induced in a gradient coil of the gradient coil assembly of FIG. 3 over a period of time for a plurality of excitation currents each having a different frequency, in accordance with an exemplary embodiment.
Figure 11:
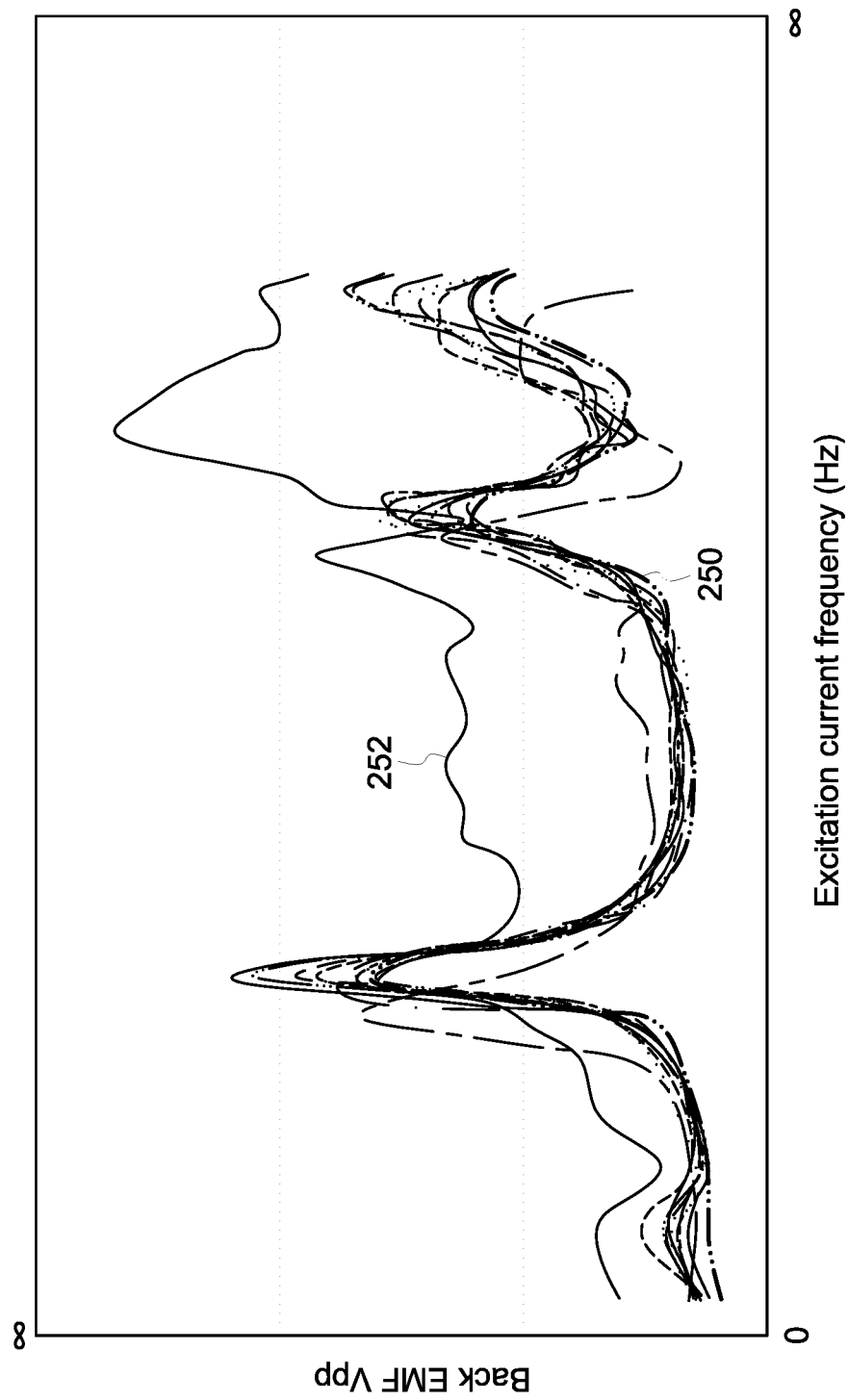
FIG. 11 is a chart depicting peak back EMF voltages of gradient coils of the gradient coil assembly of FIG. 3 for a plurality of excitation currents each having a different frequency, in accordance with an exemplary embodiment.

As illustrated in FIGS. 10 and 11, the peak voltage ("Vpp") of the back EMF voltage 202 of a gradient coil 86, 88, and/or 90 may be indicative of any experienced structural degradation. For example, FIG. 10 shows a plot of the peak voltage of a gradient coil 86, 88, and/or 90 measured at several frequencies over the course of one or more days, wherein the measurements of a particular day form a curve. As will be understood the shape of the curves (each formed by one or more peak voltage measurements over a plurality of frequencies during the same day) change overtime as the gradient coil 86, 88, and/or 90 experiences structural degradation.

Accordingly, FIG. 11 depicts a curve 250 for a gradient coil that has experienced little to no structural degradation, while curve 252 is of a gradient coil that has experienced structural degradation to the point of failure. Thus, as shown in FIG. 11, the back EMF voltage 252 of a gradient coil 86, 88, and/or 90 that has experienced a significant amount of structural degradation, i.e., a gradient coil that has failed or is about to fail, may exhibit a statistical deviation, at one or more excitation current frequencies, from the back EMF voltage 250 of a similar gradient coil 86, 88, and/or 90 that has experienced little to no structural degradation. As will be appreciated, embodiments of the present invention may determine whether a particular gradient coil 86, 88, and/or 90 has failed based at least in part on detected statistical deviations from historical norms and/or baseline data (for similar gradient coils) detected in the back EMF voltage of the gradient coil 86, 88, and/or 90. The range of the excitation current frequency and the range of the back EMF voltage may vary for different gradient coils (e.g., different designs, different manufacturers, etc.) and can be identified without undue experimentation.

Thus, in embodiments, the one or more sensors 98, 100, 102 may include a voltmeter that measures the back EMF voltage 202 in a gradient coil 86, 88, and/or 90. As will be appreciated, in embodiments, the voltmeter 98, 100, 102 may be disposed in one or more of the x, y, or z gradient amplifiers 46 as further shown in FIG. 1. Thus, in some embodiments, the sensors 98, 100, 102 may be voltmeters that measure the back EMF voltage of a gradient coil 86, 88, and/or 90 from the perspective of the gradient amplifiers 46.

While the foregoing paragraphs have discussed the one or more parameter readings 107 (FIGS. 7 and 17) as being either acoustics and/or back EMF measurements, it will be understood that, in embodiments, the obtained parameter readings 107 may include: impedance measurements; inductance measurements; resistance measurements; strain measurements; temperature measurements; acceleration measurements, e.g., the physical vibration of the gradient coil 86, 88, and/or 90; B0 drift measurements; terminal block torque measurements, e.g., strain on the terminal blocks 134 (FIG. 2) which connect the gradient coil 86, 88, and/or 90 to power cables that supply the electrical power, e.g., the excitation current 200 (FIG. 8) that excites/energizes the coil 86, 88, and/or 90; and/or other metrics appropriate for determining the structural degradation of the gradient coil 86, 88, and/or 90. Accordingly, in such embodiments, the one or more sensors 98, 100, 102 may include resistance sensors, strain gauges, temperature probes, accelerometers, current meters, and/or other types of sensors suitable for measuring the aforementioned metrics.

Figure 12:
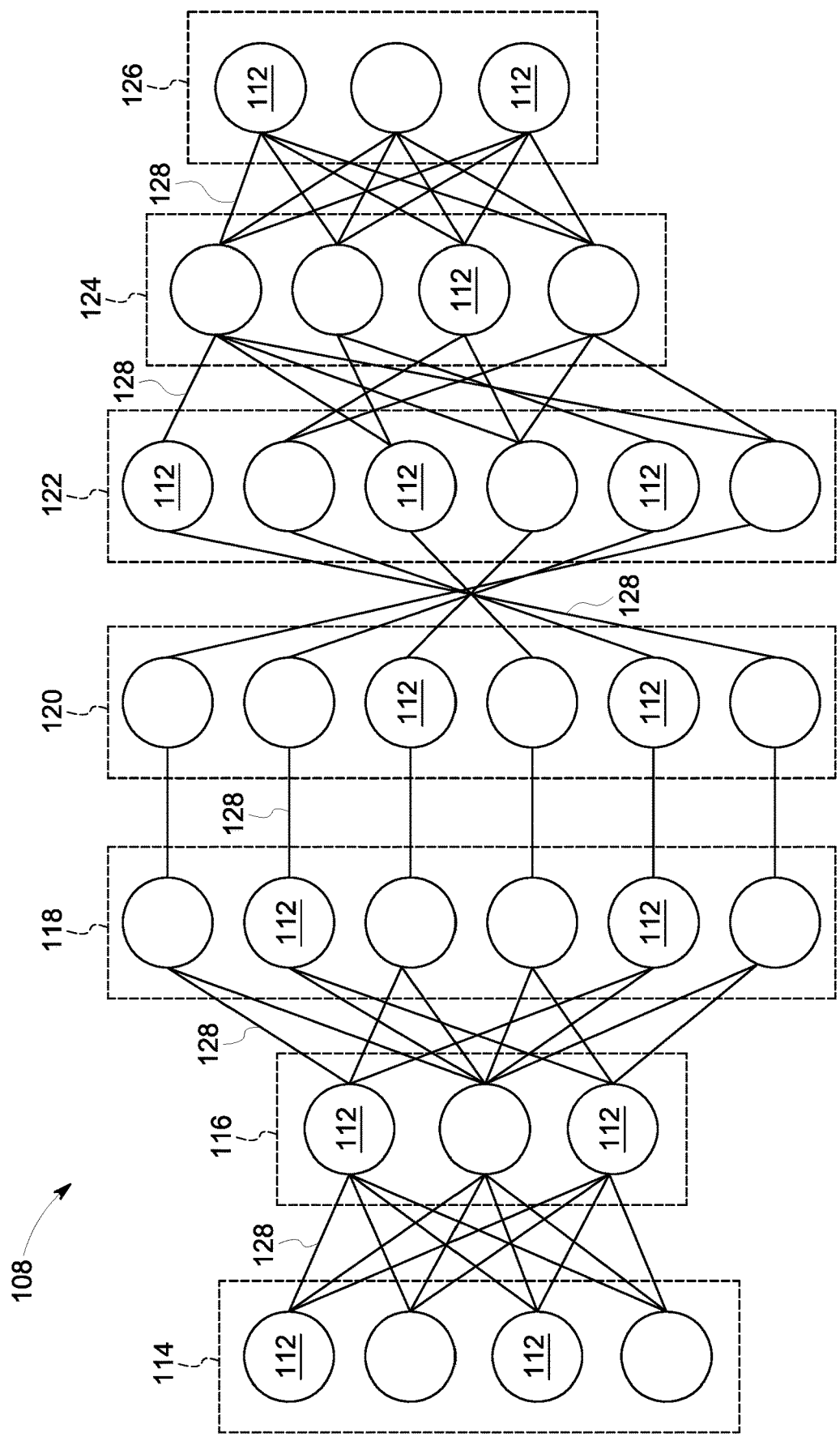
FIG. 12 is a block diagram of a neural network of the system of FIG. 7, in accordance with an exemplary embodiment.

Moving now to FIG. 12, in some embodiments, a neural network 108 is used for monitoring the health status of the gradient coil. The neural network 108 may include one or more nodes/neurons 112 which, in embodiments, may be disposed into one or more layers 114, 116, 118, 120, 122, 124, 126. As used herein with respect to a neural network, the term "layer" refers to a collection of simulated neurons that have inputs and/or outputs connected in similar fashion to other collections of simulated neurons. Accordingly, as shown in FIG. 12, the neurons 112 may be connected to each other via one or more connections 128 such that data, e.g., the parameter readings 107 (FIGS. 7 and 17) obtained from the one or more sensors 98, 100, 102 may propagate from an input layer 114, through one or more intermediate layers 116, 118, 120, 122, 124, to an output layer 126.

Figure 13:
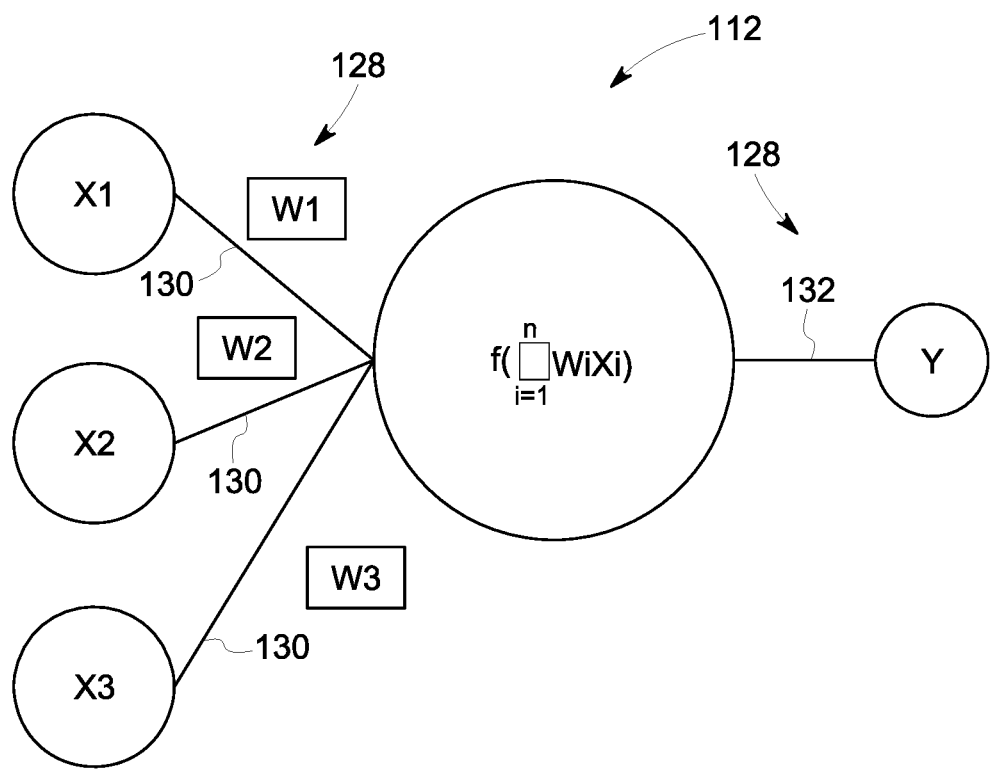
FIG. 13 is a block diagram of a neuron of the neural network of FIG. 12, in accordance with an exemplary embodiment.

As shown in FIG. 13, the connections 128 of an individual neuron 112 may include one or more input connections 130 and one or more output connections 132. Each input connection 130 of a neuron 112 may be an output connection of a preceding neuron, and the output connections 132 of the neuron 112 may be an input connection of one or more subsequent neurons. While FIG. 13 depicts a neuron 112 as having a single output connection 132, it will be understood that neurons may have multiple output connections that transmit/pass the same value. In embodiments, the neurons 112 may be data constructs, e.g., structures, instantiated class objects, matrices, etc., and the input connections 130 may be received by a neuron 112 as weighted numerical values, e.g., floating point or integer values. For example, as shown in FIG. 13, input connections X1, X2, and X3 may be weighted via weights W1, W2, and W3, respectively, summed, and sent/transmitted/passed as output connection Y. As will be appreciated, the processing of an individual neuron 112 may be represented, generally, by the equation:

$$Y = f\left(\sum_{i=1}^{n} WiXi\right)$$

where n is the total number of input connections 130 to the neuron 112. In embodiments, the value of Y may be based at least in part on whether the summation of WiXi exceeds a threshold. For example, Y may have a value of zero (0) if the summation of the weighted inputs fails to exceed a desired threshold.

Figure 14:
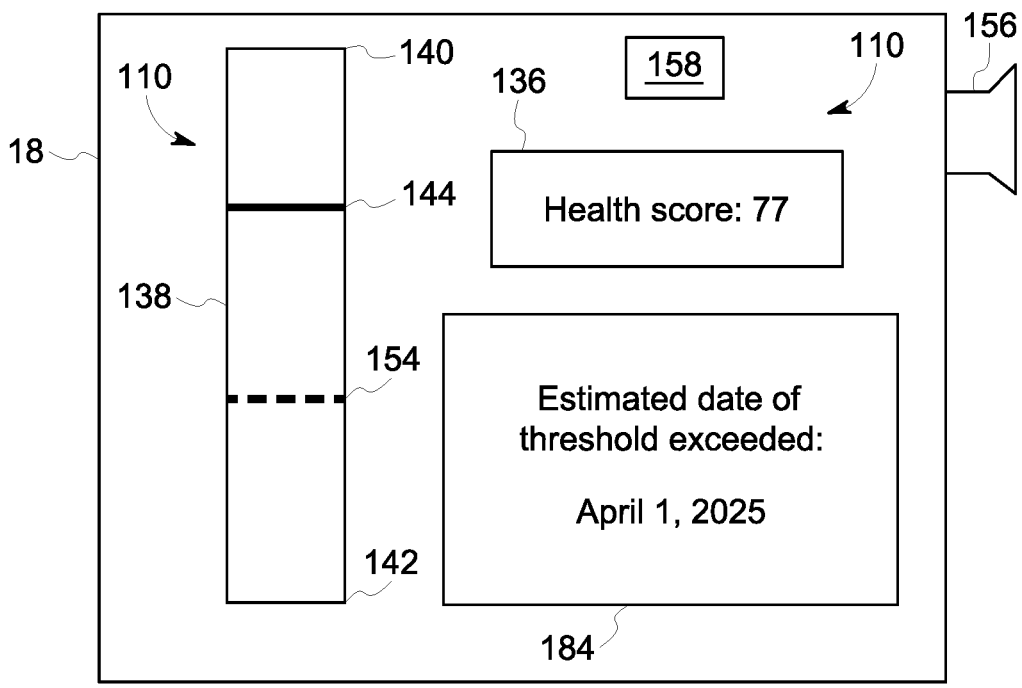
FIG. 14 is a diagram of the health status of the system of FIG. 7 as displayed on a monitor of the MRI system of FIG. 1, in accordance with an exemplary embodiment.

As will be further understood, the input connections 130 of neurons 112 in the input layer 114 (FIG. 12) may be mapped to the parameter readings 107 (FIGS. 7 and 17) obtained from the one or more sensors 98, 100, 102 (FIGS. 1 and 4-7), while the output connections 132 of the neurons 112 in the output layer 126 (FIG. 12) may be mapped to the health status 110 (FIG. 14). As used herein, "mapping" an input connection 130 to the parameter readings 107 refers to the manner by which the parameter readings 107 affect/dictate the value of the input connections 130. Similarly, as also used herein, "mapping" an output connection 132 to the health status 110 refers to the manner by which the value of the output connection 132 affects the health status 110. Accordingly, in embodiments, the parameter readings 107, or values derived therefrom, are passed/fed to the input layer 114 of the neutral network 112 and propagate through the layers 114, 116, 118, 120, 122, 124, 126 such that mapped output connections of the output layer 126 generates/corresponds to the health status 110.

For example, as shown in FIG. 14, the health status 110 may be a numerical score having a maximum and minimum value, e.g., a maximum value of one hundred (100) may indicate that the gradient coil 86, 88, and/or 90 has no detectable structural degradation, and a minimum value of zero (0) may indicate that the gradient coil 86, 88, and/or 90 has the maximum detectable structural degradation. As such, the health status 110 may be represented on the display 18 (also shown in FIG. 1) as a number (depicted by box 136), and/or via a scale 138 having a top 140 and bottom 142 respectively corresponding to the maximum and minimum score values and with a slidable bar 144 corresponding to the value of the health status 110.

Figure 15:
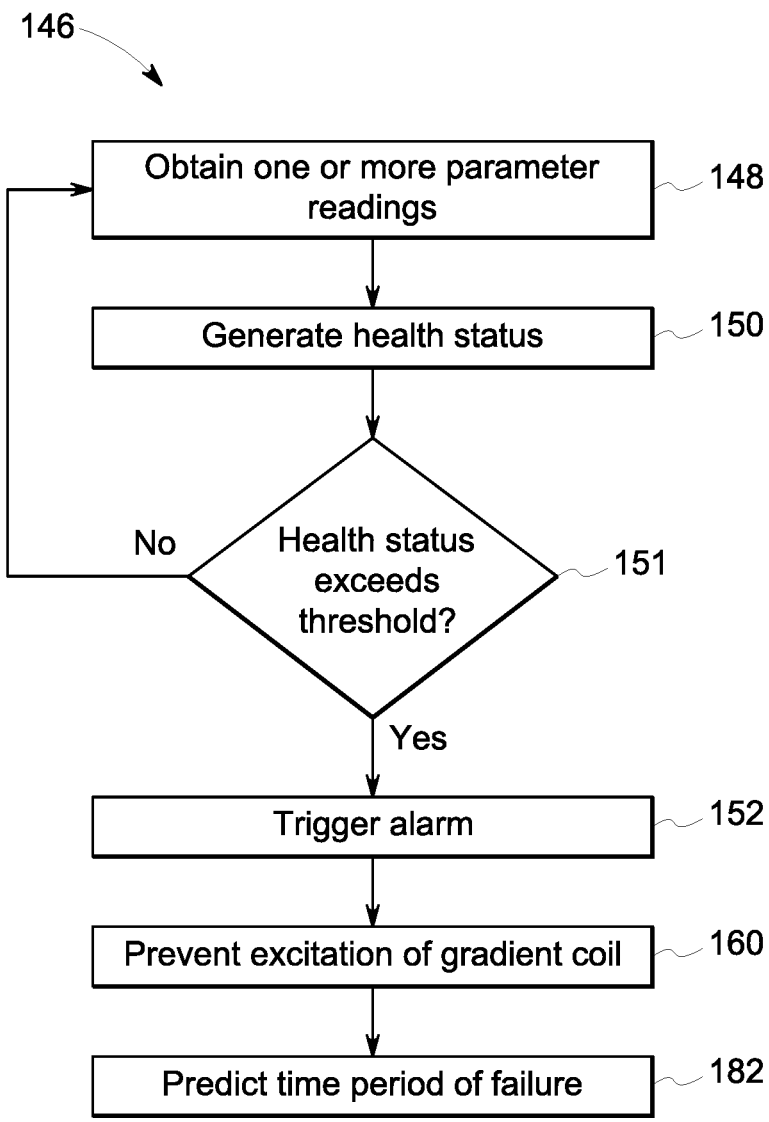
FIG. 15 is a flow chart of a method of monitoring a health status of a gradient coil disposed in the MRI system of FIG. 1 utilizing the system of FIG. 7, in accordance with an exemplary embodiment.

Turning to FIG. 15, a method 146 of monitoring the health status 110 (FIG. 14) via the system 96 (FIG. 7) according to an exemplary embodiment is shown. The method 146 includes obtaining, at step 148, the one or more parameter readings 107 (FIGS. 7 and 17) of the gradient coil 86, 88, and/or 90 (FIGS. 4-6) via the one or more sensors 98, 100, 102 (FIGS. 1 and 4-7); and generating, at step 150, the health status 110 (FIG. 14) via the neural network 108 (FIG. 12), or other model, based at least in part on the one or more parameter readings 107.

The method 146 may further include determining, at step 151, whether the generated health status 110 has exceeded a threshold 154 (FIG. 14), e.g., a lower threshold, and, optionally, triggering, at step 152, an alarm when the health status 110 (FIG. 14) exceeds the lower threshold 154. For example, in embodiments, the alarm may be an audio sound played through a speaker 156 (FIG. 14) and/or a visual cue 158 (FIG. 14) on the display 18. While the threshold 154 has been described above as a lower threshold, it will be understood that, in embodiments, the threshold 154 may be an upper threshold.

In embodiments, the method 146 may further include preventing, at step 160, via the controller 106 (FIG. 7), the excitation/energization/operation of the gradient coil 86, 88, and/or 90 when the health status 110 (FIG. 14) exceeds the lower threshold 154 (FIG. 14).

Figure 16:
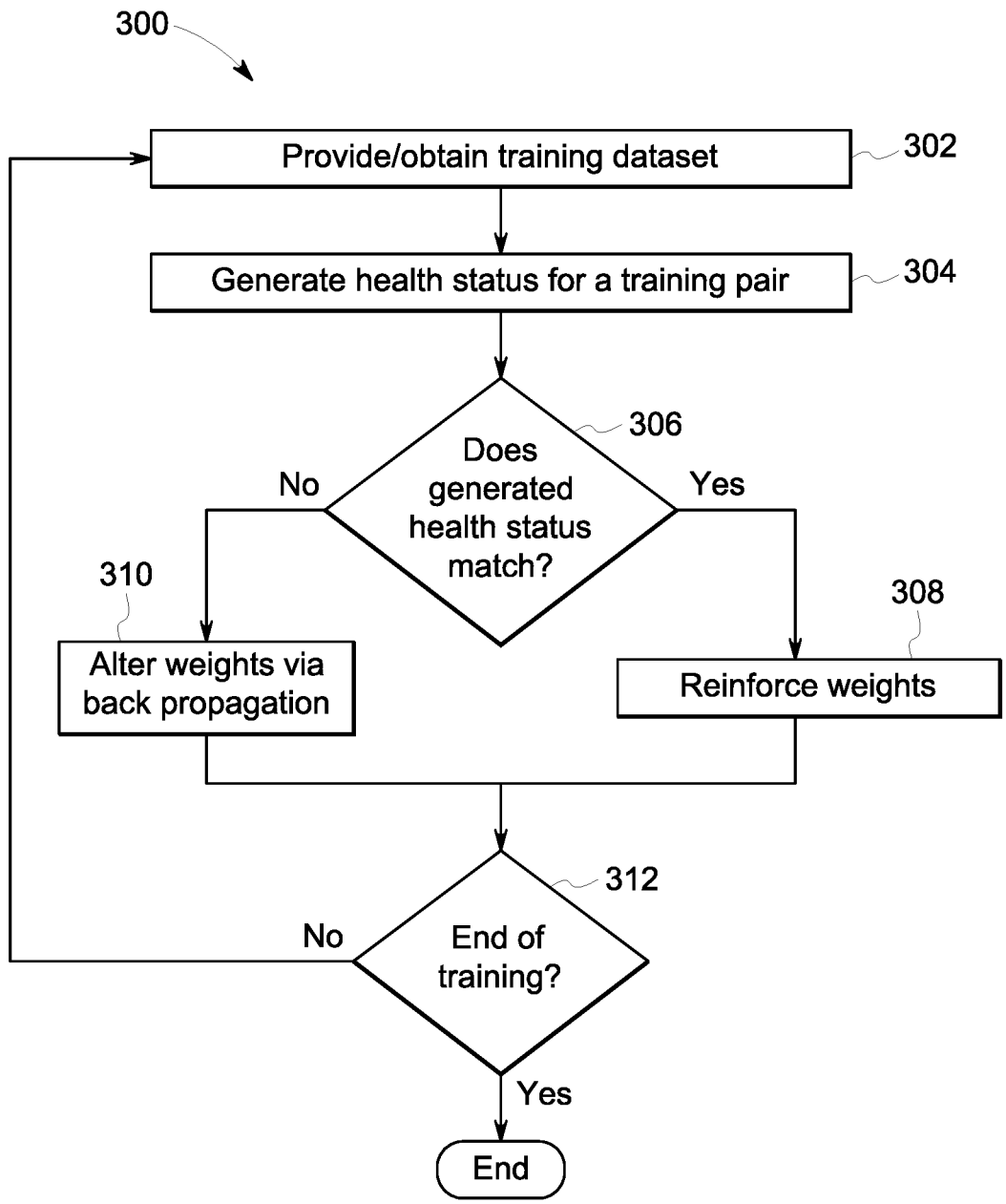
FIG. 16 is a flow chart depicting a method of training the neural network of FIG. 12, in accordance with an exemplary embodiment.

Embodiments of the present invention may also provide for methods of training the neural network 108 (FIG. 12). For example, shown in FIG. 16 is a method 300 of training the neural network 108 via supervised learning. As used herein, the term "supervised learning" refers to a process of training the weights of the neural network 108 with a dataset that has inputs with known outputs, e.g., a labeled training dataset. For example, in embodiments, the neural network 108 may be provided, at step 302, a labeled training dataset that includes one or more pairings of a parameter reading 107 (FIGS. 7 and 17) to a known health status 110 (FIG. 14), e.g., a set of recorded/acquired/sampled acoustic frequencies generated by the gradient coil 86, 88, and/or 90 paired to a corresponding set of known/expected health scores for each of the recorded/acquired/sampled acoustic frequencies. In embodiments, a health status may be generated via the neural network 108, at step 304, for each pairing within the training dataset, and compared, at step 306, to the known health status of the same pairing. The weights of the neural network 108 may then be reinforced, at step 308, or adjusted, at step 310, if the generated health status respectively matches or fails to match the known health status of the pairing. As represented by decision block 312, steps 304, 306, 308, and 310 may be repeated for all pairings in the training dataset multiple times until the accuracy of the neural network 108 reaches a sufficient level, e.g., the health status generated by the neural network 108 for a given parameter reading 107 in a pairing of the training dataset matches the known health status of the same paring ninety-nine percent (99%) of the time.

While the above paragraphs discuss training the neural network 108 via supervised methods, as will be appreciated, other methods of training the neural network 108 may be employed, e.g., unsupervised learning. As used herein, the term "unsupervised learning" refers to a process of training the weights of the neural network 108 without known outputs. For example, in such embodiments, the neural network 108 may be configured to train the weights so as to maximize a cost function.

Figure 17:
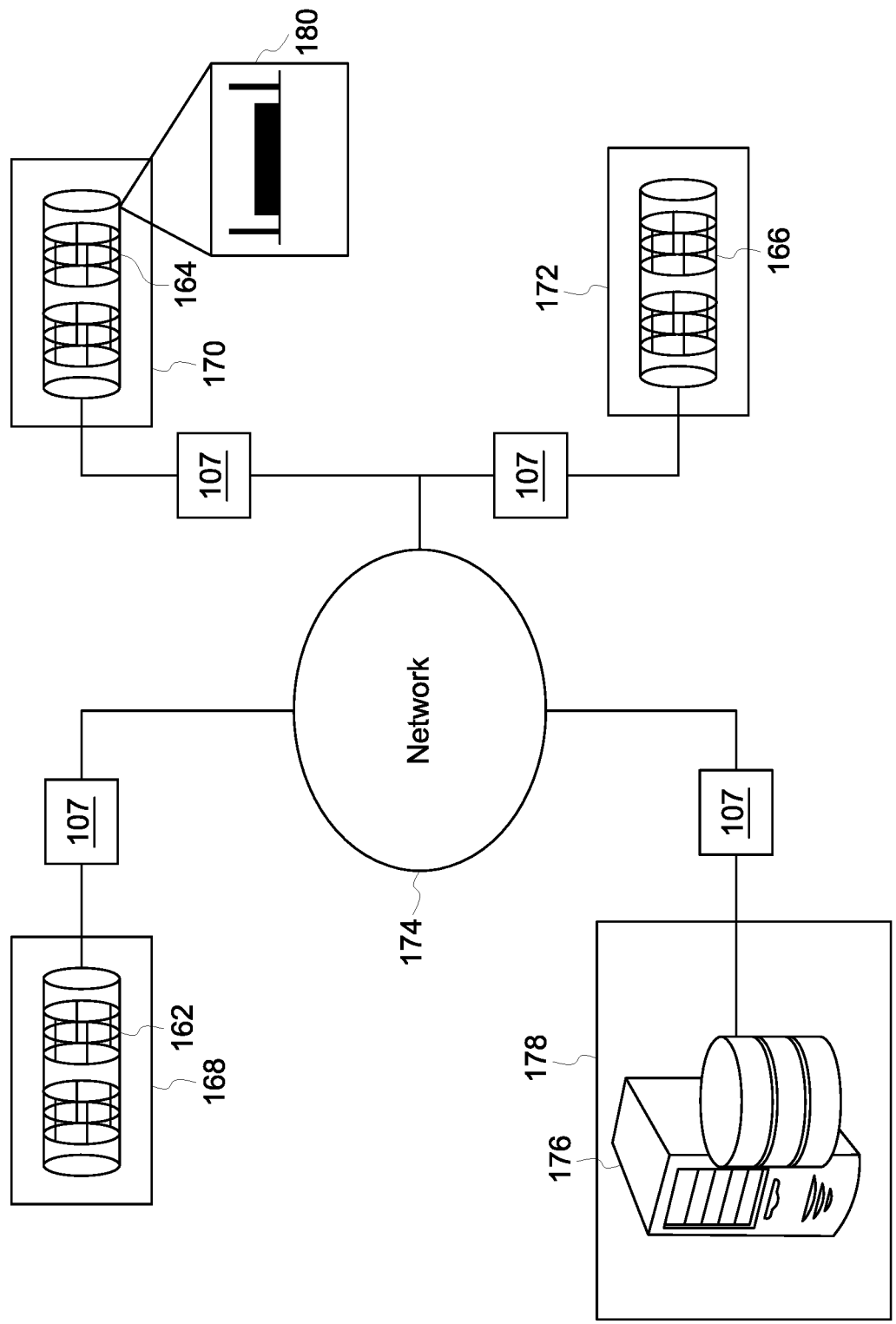
FIG. 17 is a block diagram depicting a server used to train the neural network of FIG. 12, wherein the server is networked to one or more MRI systems, in accordance with an exemplary embodiment.

Moving to FIG. 17, an instance of the neural network 108 (FIG. 12) may be trained on a dataset derived from a plurality of gradient coils, generally represented by 162, 164, 166, which may be disposed in different MRI systems, generally represented by 168, 170, 172, located at different operating facilities, e.g., hospitals and/or labs, across the world, connected via a network 174, e.g., the Internet, to a server 176 located at a separate site 178, e.g., a MRI research center and/or laboratory. As will be appreciated, each of the MRI systems 168, 170, 172 may include embodiments of the system 96 (FIG. 7) such that the training dataset may include parameter readings 107 (FIGS. 7 and 17) acquired from the gradient coils 162, 164, 166 via sensors as described above, and a corresponding list of the date/times of failures of the same gradient coils 162, 164, 166 and/or pulse sequences 180. The dataset may then be sent to, stored in, or otherwise accessible by the server 176. An instantiation of the neural network 108 may then be trained on the server 176 with the dataset in order to determine/discover relationships/symptoms within the acquired parameter readings 107 (FIGS. 7 and 17) indicative of gradient coil failures. As will be appreciated, the weights of the instantiated neural network trained on the server 176 may then be sent back to the system 96 in each of the MRI systems 168, 170, 172. In other words, the historical data, e.g., parameter readings 107 (FIGS. 7 and 17) obtained from the gradient coils 162, 164, 166 of multiple MRI systems 168, 170, 172 over a given duration of time, may be trended via the neural network 108 to detect/identify impending failures within the same, or similar, gradient coils 162, 164, 166.

For example, parameter readings 107 (FIGS. 7 and 17) may be obtained from the gradient coils 162, 164 of one or more MRI systems 168 and 170 at, or near, the time the MRI systems 168 and 170 come online, i.e., begin operational use, and stored as historical data in the server 176. The neural network 108 may then be trained to recognize typical ranges for a given parameter reading 107 that correspond to the beginning of a gradient coil life cycle, i.e., the time from first use of a gradient coil until failure. Over time, additional parameter readings 107 may be obtained from the gradient coils 162, 164 in the MRI systems 168 and 170 and stored in the server 176 so that the neural network 108 may be trained to recognize how a parameter reading 107 changes during the life cycle of a gradient coil, up to and/or including, failure of the gradient coil.

As will be appreciated, as new/younger MRI systems, e.g., MRI system 172, come online after the neural network 108 has had the opportunity to be trained on parameter readings 107 (FIGS. 7 and 17) encompassing a full life cycle of one or more gradient coils 162, 164 of the older MRI systems 168 and 170, the health status of the gradient coils 166 of the new/younger MRI systems 172 may be repeatedly generated at various points in their own life cycles via instances of the neural network 108 operating locally at the new systems 172 using training results/weights obtained/learned from the life cycles of the older gradient coils 162 and 164. For example, in such embodiments, the health status 110 may be a score that ranges from zero (0) to ten (10) where the neural network 108 generates/assigns a ten (10) for a gradient coil 166 in a new/younger MRI system 172 with parameter readings 107 (FIGS. 7 and 17) that are in accordance with historical norms for the particular point in the gradient coil's 166 life cycle, as understood/learned via the neural network 108 from training with the historical dataset/parameter readings 107 acquired from the gradient coils 162 and 164 of the older MRI systems 168 and 170.

As will be understood, in such embodiments, the neural network 108 may generate progressively lower scores corresponding to the amount that the parameter readings 107 of the gradient coil 166 in the new/younger MRI system 172 deviate from the historical norms, with zero (0) being the maximum amount of detectable deviation. In other words, in such embodiments, a health status/score 110 (FIG. 10) of ten (10) indicates that the gradient coil 166 is aging, i.e., incurring structural degradation, as expected based on historical norms, where a health status/score of zero (0) indicates that the gradient coil 166 is aging faster than expected based on historical norms. In such embodiments, the lower threshold 154 (FIG. 14) may be a score of five (5), which may indicate that the gradient coil should be replaced, and/or that corrective action should be taken to mitigate/reduce the risk of failure, e.g., a reduction in the temperature acceleration of the gradient coil during future operational cycles and/or the use of software interlocks to block-out excitation frequencies that may increase structural degradation.

Additionally, in embodiments, the neural network 108 may provide for a correlation between gradient coil acceleration, i.e., physical vibrations, and/or acoustics, and gradient coil failure; and similarly, for a correlation between inductance-and-resistance ("LR") and back EMF and gradient coil failure.

As will be appreciated, while the above described training scenario concerned parameter readings 107 (FIGS. 7 and 17) obtained from multiple MRI systems 168 and 170, it will be understood that, in embodiments, the dataset used to train the weights of the neural network 108 may be derived from a single gradient coil 86, 88, and/or 90 of a single MRI system 168.

Referring back to FIG. 15, in embodiments, the method 146 may further include predicting, at step 182, a time period 184 (FIG. 14) when the health status 110 (FIG. 14) will exceed the lower threshold 154 (FIG. 14). For example, the neural network 108 may be trained as disclosed above such that the neural network 108 is able to accurately predict, based on the acquired parameter readings 107 (FIGS. 7 and 17), a future time/date that the gradient coil 86, 88, and/or 90 will have sustained structural degradation sufficient to warrant repair and/or replacement of the gradient coil 86, 88, and/or 90. The time period 184 may be displayed on the monitor 18 (as shown in FIG. 14) in various formats, e.g., weeks, years, days, hours, minutes, seconds, standard date formats, and/or any other format capable of conveying the amount of time remaining until the health status 110 exceeds the lower threshold 154.

The use of a neural network to monitor the health status of the gradient coils 86, 88, and/or 90 is representative of one approach that can be deployed by the system 96 depicted in FIG. 7. It is understood that other systems and methods can be utilized. For example, in one embodiment, the system 96 can use a rule-based approach to analyze the parameter readings 107 obtained by the sensors 98, 100, 102 to determine whether the integrity of one or more of the coils 86, 88, 90 is structurally degraded or compromised (e.g., delamination of a coil). In this example, the memory device 104 can store a set of rules defining acceptance criteria that the data in the parameter readings 107 has to satisfy to establish that the coils are structurally sound or intact and not degraded or compromised.

In one embodiment, the parameter readings 107 obtained from one or more of the coils 86, 88, 90 by the sensors 98, 100, 102 includes a back EMF measurement as discussed above with regard to FIGS. 8-11. As noted above with respect to these figures, changing current through the imaging windings of a gradient coil when in a ramped magnet may cause the gradient coil to move and/or flex. The motion produced depends on the characteristics of the changing current (amplitude and frequency) as well as the mechanical characteristics of the gradient coil and mounting. If the gradient motion causes an imaging gradient winding to cross field lines, a counter force is created according to Lenz's Law that induces voltage on the winding. Therefore, the induced voltage is related to gradient motion which is related to the mechanical state of the gradient coil. Thus, a change in the induced voltage response of the gradient coil as a function of frequency indicates a mechanical change to the system (gradient coil or mounting). To this extent, in the embodiments that follows, the back EMF measurements are used as a surrogate for the indication of gradient coil motion in order to ascertain the structural integrity of the coils 86, 88, 90, i.e., whether the coils are structurally sound or intact, or alternatively, degraded or compromised, i.e., in a failing or a failed state by evaluating whether there are changes in the back EMF measurements. In particular, the various embodiments provide an approach that can differentiate these changes in the back EMF measurements and ascertain whether these changes are indicative of structural integrity issues.

In one embodiment, the controller 106 of the system 96 depicted in FIG. 7 can obtain the back EMF measurements from the sensors 98, 100, 102. In addition, the memory device 104 of the system 96 can store a set of rules defining acceptance criteria that the back EMF measurements have to satisfy to establish that the coils 86, 88, 90 are structurally sound or intact and not degraded or compromised. To this extent, the controller 106 can evaluate the structural integrity of the coils 86, 88, 90 as a function of the back EMF measurements and the acceptance criteria. For example, the controller 106 can apply the set of rules to the back EMF measurements in order to determine whether the back EMF measurement satisfies the acceptance criteria. If the controller 106 determines that any of the back EMF measurements obtained from any of the coils 86, 88, 90 fails to satisfy or violates the acceptance criteria, then the controller can identify the respective gradient coil as having a structural integrity issue. The status of the structural integrity of the coils as ascertained from the evaluation can be issued through any of a number of known reporting mechanisms including, but not limited to, generating a report, disseminating a warning (e.g., an alarm), etc. In this manner, the gradient coil can be removed from further use in the MRI system if the evaluation is conducted with a system that is installed and operational at a clinical site. In another scenario, if the evaluation occurs at a manufacturing site of the MRI system, then the coil can be discarded and not installed in the MRI system in response to an evaluation that the coil violates the acceptance criteria. Further details of the evaluation of the back EMF measurements with the set of rules including the acceptance criteria are elaborated below.

Figure 18:
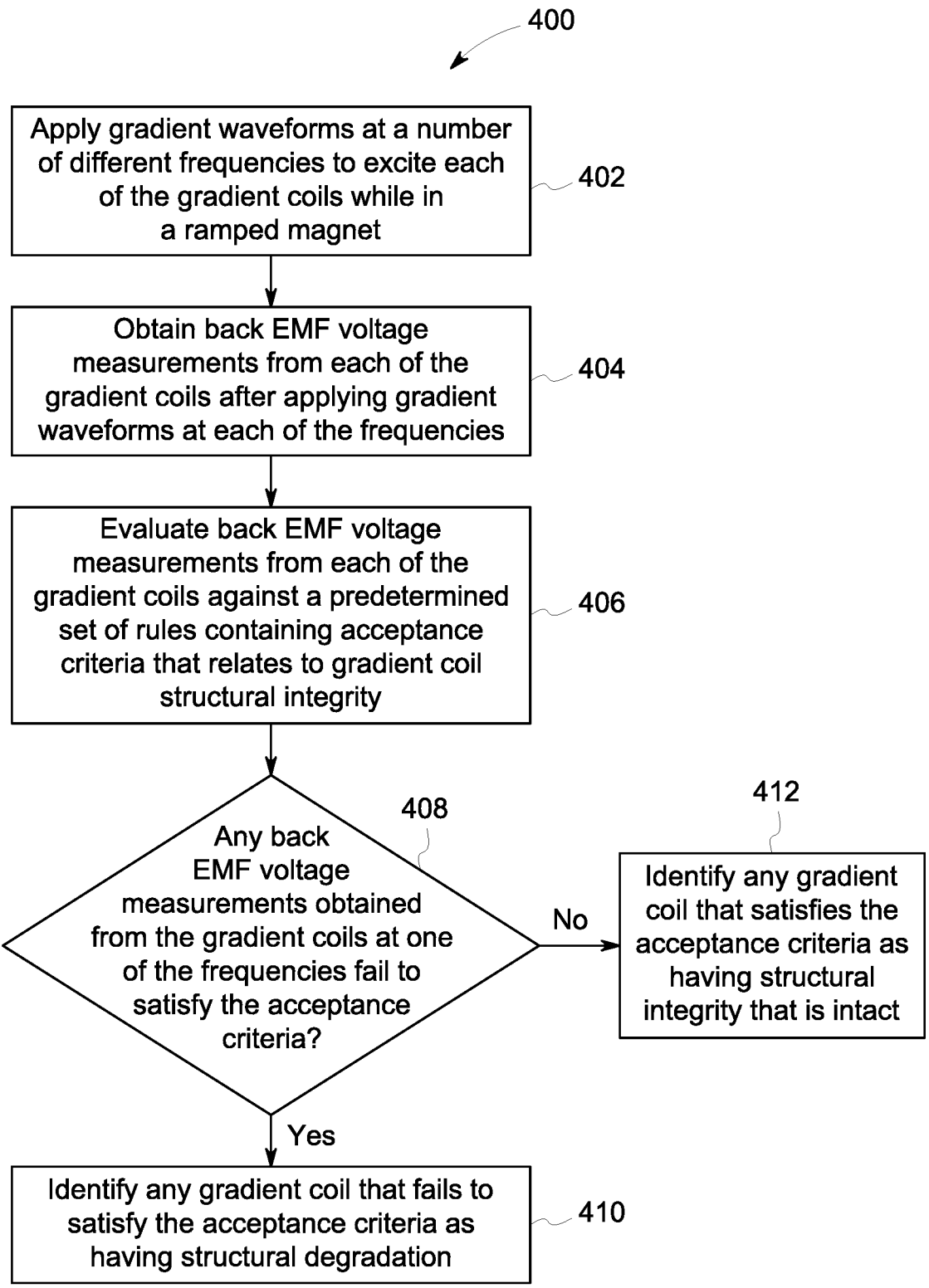
FIG. 18 is a flow chart depicting the operations of a rule-based approach for evaluating the structural integrity of the gradient coils disposed in the MRI system of FIG. 1 based on back electromotive force (EMF) measurements obtained from the coils, in accordance with an exemplary embodiment.

FIG. 18 is a flow chart 400 depicting the operations of a rule-based approach for evaluating the structural integrity of any of the gradient coils disposed in the MRI system of FIG. 1 based on back EMF measurements obtained from the coils. In one embodiment, these operations can be performed on gradient coils that are installed and operational in an MRI system that is operating in a clinical environment as part of a test or a maintenance investigation. In another embodiment, the operations can be performed in a manufacturing environment in which the coils are tested as part of the production process before installation of the coils into an MRI system, and prior to shipping of the MRI system to a clinical site.

The operations of the flow chart 400 begin by applying and removing an excitation current to the gradient coils 86, 88, and 90. In particular, as shown in operation 402 of FIG. 18, the applying and removing of an excitation current to the gradient coils 86, 88, and 90 can include applying gradient waveforms representative of this excitation current at a number of different frequencies that is specific to excite each of the coils while in a ramped magnet. In one embodiment, the gradient amplifier 46 can apply and remove the excitation current to the gradient coils 86, 88, and 90 at the different frequencies. These waveforms which represent the excitation current and the back EMF measurements at particular frequencies can take the form of any of a number of shapes. For example, the shapes of the waveforms can include but are not limited to, sinusoidal and bipolar trapezoid waveforms. In a preferred embodiment, the waveforms can include sine waves that last a predetermined amount of time for each frequency over a predetermined range of frequencies that increments in predefined steps throughout the range. In one embodiment, the waveforms can include sine waves lasting approximately 170 msec, with frequencies ranging from 500-2000 Hz in 10 Hz steps. It is understood that the other time periods, frequency ranges and steps can be selected, and thus, this example is not meant to be limiting.

The sensors 98, 100, 102 can obtain the back EMF measurements, which as noted above can alternatively be referred to as back EMF voltage measurements, over the full range of frequencies and provide the measurements to the controller 106 for evaluation. With reference to the flow chart 400 of FIG. 18, this operation is embodied at 404 where the back EMF voltage measurements from each of the gradient coils are obtained after applying the gradient waveforms at each of the frequencies. In general, during this operation, the gradient amplifier 46 pulses the gradient coils 86, 88, and 90 with the gradient waveforms at each frequency, the sensors 98, 100, 102 obtain the back EMF measurements and forwards the measurements to the controller 106. This pulsing and measuring of the gradient coils 86, 88, and 90 is performed at each of the different frequencies while moving over each of locations along the corresponding axes of the coils.

At 406, the controller 106 evaluates the back EMF voltage measurements from each of the gradient coils against a predetermined set of rules containing acceptance criteria that relates to gradient coil structural integrity. The acceptance criteria, which is explained below in more detail, specifies predefined requirements for the amplitudes of the back EMF measurements for each of the frequencies that were measured. In an embodiment, the acceptance criteria is established from a population or a plurality of gradient coils having structural integrity deemed sound and intact. In general, this acceptance criteria is derived from back EMF measurements obtained from the population of gradient coils over the full range of frequencies that are tested and measured in the flow chart 400.

If the controller 106 determines at 408 that any of the back EMF voltage measurements obtained from the gradient coils 86, 88, and 90 at any of the frequencies fails to satisfy the acceptance criteria, then the corresponding coil with the violation of the acceptance criteria is identified at 410. Alternatively, if the controller 106 determines at 408 that the back EMF voltage measurements obtained from the gradient coils 86, 88, and 90 at all of the frequencies satisfy the acceptance criteria, then each of the coils is identified at 412 as having acceptable structural integrity (i.e., the coils are deemed structurally sound and intact). In general, a single failure of any one of the gradient coils 86, 88, and 90 at one of the frequencies is indicative of a complete failure of a coil. However, it is understood that if there is only a minimal amount of failures for a gradient coil over the range of frequencies, then it may be possible to make a refinement to the coil in order to avoid discarding the coil. Those skilled in the art will appreciate that the extent of the failures and the degree to the amount of violation between the back EMF measurements and acceptance criteria are some of the factors that can determine whether refinement of the gradient coil is a suitable option as opposed to discarding the coil.

While for purposes of simplicity of explanation, the operations shown in FIG. 18 are described as a series of acts that can be implemented as an automated script. It is to be understood and appreciated that the operations associated with FIG. 18 are not limited by the order of acts, as some acts may, in accordance therewith, occur in a different order and/or concurrently with other acts from that shown and described herein. For example, those skilled in the art will understand and appreciate that a methodology or operations depicted in FIG. 18 could alternatively be represented as a series of interrelated states or events, such as in a state diagram. Moreover, not all illustrated acts may be required to implement a methodology in accordance with the subject innovation. Furthermore, interaction diagram(s) may represent methodologies, or methods, in accordance with the subject disclosure when disparate entities enact disparate portions of the methodologies. Further yet, two or more of the disclosed example methods can be implemented in combination with each other, to accomplish one or more features or advantages described herein.

Although the above paragraphs discuss the evaluation of the structural integrity of the gradient coils as a computer-implemented process, it is understood that not all aspects of this evaluation should be limited to the use of a computer system to facilitate the evaluation described in the various embodiments. For example, the decision of whether the gradient coils have sound or intact structural integrity can include a person evaluating the data as opposed to a computer system.

As noted previously, the acceptance criteria can be established from back EMF measurements obtained from a population of gradient coils deemed to have acceptable structural integrity that is solid and intact. Generally, a population of at least 10 to 20 gradient coils should be a sufficient number of coils to obtain back EMF measurements that can be used to derive the acceptance criteria. These back EMF measurements are generally collected over a full range of frequencies that could be used to test the gradient coils. In addition to collecting the back EMF measurements over the full range of frequencies, these measurements can also be classified according to the type of gradient coil (i.e., x-gradient coil, y-gradient coil, and z-gradient coil).

The application of the gradient waveforms to each of the gradient coils in a population of coils over a range of frequencies, collection of back EMF measurements from the coils, compilation of the results, and derivation of the acceptance criteria from the results for each of the frequencies are functions that those skilled in the art can perform using any of a number of well-known data collection and analyzation techniques familiar to those skilled in collecting and analyzing data from MRI systems. For example, the acceptance criteria can be established by developing a statistical distribution from the back EMF measurements obtained from the population of structurally sound or intact gradient coils. Based on the statistical distribution of the back EMF measurements from the population of structurally sound or intact gradient coils, the acceptance criteria can then be set based on the values of the back EMF measurements. For example, the failure limit could be set at a mean value from a set of known good gradient back-EMF measurements plus 1-3 standard deviations for each of the frequencies.

After the acceptance criteria has been established, then the rules can be stored in the memory device 104 of the system 96 depicted in FIG. 7. In this manner, the sensors 98, 100, 102 can collect the back EMF measurements from the gradient coils 86, 88, and 90 and forward the data to the controller 106. The controller 106 can then apply the back EMF measurements obtained from the gradient coils 86, 88, and 90 against the acceptance criteria embodied by the set rules stored in the memory device 104 to evaluate the structural integrity of the coils.

In one embodiment, the acceptance criteria that is established excludes back EMF measurements that correspond with regions near mechanical resonance frequencies of the gradient coil. As used herein, regions near mechanical resonance frequencies means within several bandwidths of the resonance frequency where the mechanical resonance bandwidth is defined by the full width half maximum of the mechanical resonance.

It has been determined that excluding regions near mechanical resonance frequencies can make the structural integrity evaluation more robust because there is more variability associated with the measurements around these regions of mechanical resonance frequencies due to factors that can include, but are not limited to the magnet type deployed in the MRI system and the mounting of the gradient coils. This variability in the measurements around these regions of mechanical resonance frequencies makes it more likely that the structural integrity evaluation can have "false positives", i.e., that is identify a structurally sound coil as one that is structurally compromised or degraded. By excluding the mechanical resonance frequencies from the acceptance criteria, and focusing on regions that are more stable, any instances of measurements that violate the criteria are considered better indicators of a compromised or degraded gradient coil because the variability of the mechanical resonance frequencies has been removed from the evaluation. Accordingly, by focusing on frequencies in regions that are between the mechanical resonance resonances, then there will be greater specificity with the back EMF measurements, which obviates the structural integrity evaluation having "false positives" which could lead to the needless removal of structurally sound gradient coils. In addition, removing the regions of mechanical resonance resonances from the acceptance criteria not only improves the specificity of the back EMF measurements, but also increases the repeatability of the measurements which further reducing the risk of the evaluation having "false positives."

In an embodiment in which mechanical resonance frequencies are excluded, the acceptance criteria can comprise a single rule. For example, the acceptance criteria in this embodiment can include a peak back EMF voltage upper specification limit that is less than or equal to a mean plus a predetermined standard deviation of peak back EMF voltage measurements obtained from the population or plurality of known gradient coils with acceptable structural integrity. The predetermined standard deviation used with this acceptance criteria can include but is not limited to 3, 5 and 7 standard deviation. However, it is understood that other standards of deviation can be utilized, and thus the embodiments of the present invention should not be limited to any particular standard of deviation.

FIG. 19 is an example 500 illustrating an evaluation of the structural integrity of a gradient coil using acceptance criteria that excludes back EMF measurements that correspond with regions near mechanical resonance frequencies of the gradient coil. In this example, the graph 502 is a frequency-dependent plot of back EMF measurements (peak-to-peak voltage (Vpp)) that correlates with a larger degree of motion of the gradient coil. The lines 504 represent a number of data sets (e.g., 105) collected from a population of gradient coils (e.g., 35) known to have acceptable gradient integrity over a range of frequencies listed in table 506. The variability of the back EMF measurements is represented by the distance between dashed lines 508. As shown in the graph 502, the variability increases around mechanical resonance frequencies (e.g., ~1000 Hz) relative to regions between mechanical resonances (e.g., 700 Hz). The line 510 represents rule-based acceptance criteria that includes low frequency mechanical resonances, while the lines 512 represent rule-based acceptance criteria that excludes mechanical resonance frequencies.

In this particular example 500, the evaluated gradient coil represented by the line 514 fails to meet the acceptance criteria represented by line 510, which would likely be interpreted by a human observer, as "good" coil, i.e., a coil with structural integrity that is sound or intact. On the other hand, the acceptance criteria represented by line 512, which excludes the mechanical resonance frequencies would identify the gradient coils as a compromised or degraded coil due to the measurements associated with the evaluated coil violating the acceptance criteria of line 512. In this example, the acceptance criteria represented by line 512 that excludes the mechanical resonance frequencies would include frequency points in the following ranges: 100 Hz to 300 Hz, 435 Hz to 518 Hz, and 635 Hz to 900 Hz. The acceptance criteria that is used to evaluate the gradient coil for structural integrity is a Vpp upper specification limit the mean+ 7*standard deviation of measurements from known good coils.

Since the evaluation approach that excludes the mechanical resonance frequencies does not utilize all of the available data in the assessment of gradient coil health (i.e., the structural integrity), it may be desirable to provide specific acceptance criteria that utilizes back EMF measurements in regions that include mechanical resonance frequencies and regions that are between the mechanical resonance frequencies in order to improve sensitivity of the evaluation. Accordingly, in one embodiment, the acceptance criteria comprises predefined requirements for back EMF measurements that correspond with regions of mechanical resonance frequencies of the gradient coil and regions of back EMF measurements that correspond with other frequencies between the mechanical resonance frequencies. In this embodiment, the predefined requirements for the regions of mechanical resonance frequencies can have a more lenient acceptance criteria to account for the variability that is associated with these regions.

For example, the predefined requirement for back EMF measurements that corresponds with regions of mechanical resonance frequencies can comprises a peak back EMF voltage upper specification limit that is equal to a predetermined variability mitigation multiplier applied to a mean plus a predetermined standard deviation of peak back EMF voltage measurements obtained from a plurality of known gradient coils with acceptable structural integrity. The variability mitigation multiplier in this specification limit provides an extra cushion (e.g., 10%) to account for the variation in the mechanical resonance frequencies. In addition, the predetermined standard deviation that is utilized can be increased to provide further leeway in order to account for the regions of mechanical resonance frequencies.

The predefined requirement for back EMF measurements that corresponds with frequencies between the mechanical resonance frequencies can comprise acceptance criteria like that discussed above. For example, the predefined requirement for the regions between the mechanical resonance frequencies can comprise a peak back EMF voltage upper specification limit that is equal to a mean plus a predetermined standard deviation of peak back EMF voltage measurements obtained from a plurality of known gradient coils with acceptable structural integrity.

FIG. 20 is an example 600 illustrating an evaluation of the structural integrity of a gradient coil using acceptance criteria that includes back EMF measurements that correspond with regions of mechanical resonance frequencies of the gradient coils and regions that are between mechanical resonance frequencies. In this example 600, like in FIG. 19, the graph 502 is frequency-dependent plot of back EMF measurements (peak-to-peak voltage (Vpp)) that correlates with a larger degree of motion of the gradient coil. The lines 504 represent a number of data sets collected from a population of gradient coils known to have acceptable gradient integrity over a range of frequencies listed in table 506. The variability of the back EMF measurements is represented by the distance between dashed lines 508. As shown in the graph 502 of the example 600 in FIG. 20, the variability increases around mechanical resonance frequencies (e.g., ~1000 Hz) relative to regions between mechanical resonances (e.g., 700 Hz). The line 510 represents rule-based acceptance criteria that includes low frequency mechanical resonances, while the lines 512 represent rule-based acceptance criteria that excludes mechanical resonance frequencies. In the example 600, the evaluated gradient coil represented by the line 514 satisfies the acceptance criteria represented by both lines 510 and 512 in regions that include mechanical resonance frequencies and regions that are between the mechanical resonance frequencies.

The benefits to the aforementioned rule-based approach for evaluating the structural integrity of the gradient should be apparent from the various embodiments described herein. In particular, these embodiments provide solutions to the technical problem of evaluating the structural integrity of a gradient coil utilized in an MRI system that include providing savings in terms of time and costs in evaluating a coil. The savings in terms of time and costs that can be realized with the automated approach for evaluating the structural integrity of a gradient coil as described in these embodiment can be realized in remote monitoring and diagnostics of the coil by obviating the need to send a technician to the site of the MRI system to determine the health of the coil. Furthermore, this structural integrity evaluation can be utilized during production of the MRI system to ensure that the system is installed with gradient coils that are not structurally degraded or compromised.

Finally, it is also to be understood that the systems 10 and/or 96 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the systems 10 and/or 96 may include at least one processor and system memory/data storage structures, which may include random access memory (RAM) and read-only memory (ROM). The at least one processor of the systems 10 and/or 96 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts a controller to perform the methods disclosed herein may be read into a main memory of the at least one processor from a computer readable medium, e.g., a medium that provides or participates in providing instructions to the at least one processor of the systems 10 and/or 96 (or any other processor of a device described herein) for execution. Such a medium may take many forms, including but not limited to, non-volatile media and volatile media.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

Accordingly, by providing automated monitoring of a health status of a gradient coil, some embodiments of the present invention may reduce the risk of the gradient coil failing during an MRI scan without the need to manually inspect the gradient coil. As will be appreciated, such embodiments may improve the patient throughput of an MRI system by avoiding the need to rescan a patient due to a failed gradient coil, as well as reducing and/or avoiding down time of an MRI system incurred during manual inspection of the gradient coils.

Further, by predicting a time period during which a gradient coil is expected to fail, some embodiments of the present invention may provide for improved patient throughput over traditional MRI systems by facilitating improved coordination between scheduling patient scans and MRI system down time due to gradient coil maintenance/replacement. In other words, some embodiments of the present invention provide for proactive maintenance of gradient coils, as opposed reactively detecting an already failed gradient coil. In such embodiments, proactive maintenance of gradient coils may improve patient safety/comfort by reducing the risk that a patient will be exposed to excessive gradient coil noise/vibrations.

Further still, by using the gradient amplifiers of an MRI system to obtain back EMF parameter readings, some embodiments of the present invention provide for a system of monitoring the health status of a gradient coil that makes use of existing sensors/equipment presently found in many MRI systems. Thus, such embodiments of the present invention provide for improved monitoring of the health status of a gradient coil without incurring the significant costs typically associated with developing and/or installing new types of sensors into existing MRI systems already in use at various locations.

Yet further still, by storing and analyzing historical dataset/parameter readings, of gradient coils in multiple MRI systems, in a server, some embodiments of the invention may provide for improved understanding of future gradient coil failures. For example, in such embodiments, analysis of the historical data of the acceleration history of a failed gradient coil by the neural network may facilitate faster identification of the root cause of the failure.

In addition to any previously indicated modification, numerous other variations and alternative arrangements may be devised by those skilled in the art without departing from the spirit and scope of this invention, and the appended claims are intended to cover such modifications and arrangements. Thus, while the invention has been described above with particularity and detail in connection with what is presently deemed to be the most practical and preferred aspects, it will be apparent to those of ordinary skill in the art that numerous modifications, including, but not limited to, form, function, manner of operations, and/or use may be made without departing from the principles and concepts set forth herein.

Finally, the examples and embodiments used herein are meant to be illustrative only and should not be construed to be limiting in any manner.

What is claimed is:

1. A system, comprising:
a sensor operative to obtain a parameter reading of a gradient coil disposed in a magnetic resonance imaging system, wherein the parameter reading includes a back electromotive force (back EMF) measurement induced by movement of the gradient coil within a magnetic field provided by the magnetic resonance imaging system; and
a controller configured to obtain the back EMF measurement from the sensor and evaluate the structural integrity of the gradient coil as a function of the back EMF measurement; and
a memory device storing a set of rules defining acceptance criteria for back EMF measurements obtained from the gradient coil that are indicative of a structurally sound gradient coil;
wherein the controller is configured to report a status of the structural integrity of the gradient coil to a system user.

2. A method, comprising:
Obtaining via one or more sensors a parameter reading of a gradient coil disposed in a magnetic resonance imaging system, wherein the parameter reading includes a back electromotive force (back EMF) measurement induced by movement of the gradient coil within a magnetic field provided by the magnetic resonance imaging system;
evaluating structural integrity of the gradient coil as a function of the back EMF measurement;
retrieving a set of rules defining acceptance criteria for back EMF measurements obtained from the gradient coil that are indicative of a structurally sound gradient coil; and
reporting a status of the structural integrity of the gradient coil to a system user.

3. The system of claim 1, wherein the controller is configured to apply the set of rules in the memory device to the back EMF measurement and determine whether the back EMF measurement satisfies the acceptance criteria.

4. The system of claim 3, wherein the controller is configured to identify the gradient coil as having a structural integrity issue in response to a determination that the back EMF measurement fails to satisfy the acceptance criteria.

5. The system of claim 1, wherein the acceptance criteria excludes back EMF measurements that correspond with regions near mechanical resonance frequencies of the gradient coil.

6. The system of claim 5, wherein the acceptance criteria comprises a peak back EMF voltage upper specification limit that is less than or equal to a mean plus a predetermined standard deviation of peak back EMF voltage measurements obtained from a plurality of known gradient coils with acceptable structural integrity.

7. The system of claim 1, wherein the acceptance criteria comprises predefined requirements for back EMF measurements that correspond with regions of mechanical resonance frequencies of the gradient coil and regions of back EMF measurements that correspond with other frequencies between the mechanical resonance frequencies.

8. The system of claim 7, wherein the predefined requirement for back EMF measurements that corresponds with regions of mechanical resonance frequencies comprises a peak back EMF voltage upper specification limit that is equal to a predetermined variability mitigation multiplier applied to a mean plus a predetermined standard deviation of peak back EMF voltage measurements obtained from a plurality of known gradient coils with acceptable structural integrity.

9. The system of claim 7, wherein the predefined requirement for back EMF measurements that corresponds with frequencies between the mechanical resonance frequencies comprises a peak back EMF voltage upper specification limit that is equal to a mean plus a predetermined standard deviation of peak back EMF voltage measurements obtained from a plurality of known gradient coils with acceptable structural integrity.

10. The system of claim 1, wherein the acceptance criteria is established from a plurality of structurally sound gradient coils.

11. The system of claim 1, wherein the back EMF measurement is representative of the movement of the gradient coil within a magnetic field.

12. The method of claim 2, further comprising applying the set of rules to the back EMF measurement and determining whether the back EMF measurement satisfies the acceptance criteria.

13. The method of claim 2, wherein the acceptance criteria excludes back EMF measurements that correspond with regions near mechanical resonance frequencies of the gradient coil.

14. The method of claim 13, wherein the acceptance criteria comprises a peak back EMF voltage upper specification limit that is less than or equal to a mean plus a predetermined standard deviation of peak back EMF voltage measurements obtained from a plurality of known gradient coils with acceptable structural integrity.

15. The method of claim 2, wherein the acceptance criteria comprises predefined requirements for back EMF measurements that correspond with regions of mechanical resonance frequencies of the gradient coil and regions of back EMF measurements that are between the mechanical resonance frequencies.

16. The method of claim 15, wherein the predefined requirement for back EMF measurements that corresponds with regions of mechanical resonance frequencies comprises a peak back EMF voltage upper specification limit that is equal to a predetermined variability mitigation multiplier applied to a mean plus a predetermined standard deviation of peak back EMF voltage measurements obtained from a plurality of known gradient coils with acceptable structural integrity, and wherein the predefined requirement for back EMF measurements that corresponds with regions in between mechanical resonance frequencies comprises a peak back EMF voltage upper specification limit that is equal to a mean plus a predetermined standard deviation of peak back EMF voltage measurements obtained from a plurality of known gradient coils with acceptable structural integrity.

17. The method of claim 12, further comprising identifying the gradient coil as having a structural integrity issue in response to a determination that the back EMF measurement fails to satisfy the acceptance criteria.

18. A non-transitory computer-readable medium having stored thereon executable instructions that, in response to execution, cause a system comprising at least one processor to perform operations directed to evaluating the structural integrity of a gradient coil disposed in a magnetic resonance imaging system, the operations comprising:

obtaining via one or more sensors a parameter reading of the gradient coil disposed in the magnetic resonance imaging system, wherein the parameter reading includes a back electromotive force (back EMF) measurement induced by movement of the gradient coil within a magnetic field provided by the magnetic resonance imaging system;

evaluating the structural integrity of the gradient coil as a function of the back EMF measurement;

retrieving a set of rules defining acceptance criteria for back EMF measurements obtained from the gradient coil that are indicative of a structurally sound gradient coil; and reporting a status of the structural integrity of the gradient coil to a system user.

* * * * *